(12) United States Patent
Barrett et al.

(10) Patent No.: US 8,731,958 B2
(45) Date of Patent: May 20, 2014

(54) ADMINISTERING OF MEDICATION

(75) Inventors: John Todd Barrett, Madison, MS (US);
Fredrick Patrick Schoville, Brighton, MI (US); Spencer K Barrett, Madison, MS (US)

(73) Assignee: Advantage Pharmacy Services LLC, Madison, MS (US)

( * ) Notice: Subject to any disclaimer, the term of this patent is extended or adjusted under 35 U.S.C. 154(b) by 302 days.

(21) Appl. No.: 12/554,439

(22) Filed: Sep. 4, 2009

(65) Prior Publication Data
US 2010/0114367 A1 May 6, 2010

Related U.S. Application Data

(60) Provisional application No. 61/110,321, filed on Oct. 31, 2008.

(51) Int. Cl.
*G06Q 50/00* (2012.01)

(52) U.S. Cl.
USPC .......................................................... 705/2

(58) Field of Classification Search
USPC ...................... 194/217; 340/825.49; 364/413; 700/242; 705/2, 3
See application file for complete search history.

(56) References Cited

U.S. PATENT DOCUMENTS

| | | | |
|---|---|---|---|
| 4,695,954 A * | 9/1987 | Rose et al. | 221/15 |
| 5,883,806 A | 3/1999 | Meador et al. | |
| 5,941,363 A * | 8/1999 | Partyka et al. | 194/217 |
| 6,175,779 B1 * | 1/2001 | Barrett | 700/242 |
| 6,318,051 B1 | 11/2001 | Preiss | |
| 6,330,957 B1 | 12/2001 | Bell-Greenstreet | |
| 6,604,019 B2 | 8/2003 | Ahlin et al. | |
| 6,650,964 B2 | 11/2003 | Spano, Jr. et al. | |
| 6,671,579 B2 | 12/2003 | Spano, Jr. et al. | |
| 6,681,549 B1 | 1/2004 | Zhao et al. | |
| 6,682,156 B2 | 1/2004 | Herrington | |
| 6,985,870 B2 | 1/2006 | Martucci et al. | |
| 6,990,317 B2 | 1/2006 | Arnold | |
| 7,006,876 B2 | 2/2006 | Ross | |
| 7,006,893 B2 | 2/2006 | Hart et al. | |
| 7,142,944 B2 | 11/2006 | Holmes et al. | |
| 7,151,982 B2 | 12/2006 | Liff et al. | |
| 7,154,397 B2 | 12/2006 | Zerhusen et al. | |
| 7,155,306 B2 | 12/2006 | Haitin et al. | |
| 7,175,081 B2 | 2/2007 | Andreasson et al. | |
| D541,558 S | 5/2007 | Meyer et al. | |
| 7,264,136 B2 | 9/2007 | Willoughby et al. | |
| 7,293,558 B2 | 11/2007 | Ambrico | |
| 7,293,672 B2 | 11/2007 | Mori et al. | |
| 7,293,673 B2 | 11/2007 | Savage et al. | |
| 7,685,004 B2 | 3/2010 | Moncrief et al. | |
| 7,698,019 B2 | 4/2010 | Moncrief et al. | |
| 2005/0049747 A1 | 3/2005 | Willoughby et al. | |
| 2006/0149416 A1 * | 7/2006 | Mohapatra et al. | 700/242 |
| 2007/0226009 A1 * | 9/2007 | Hicks | 705/2 |
| 2008/0316045 A1 * | 12/2008 | Sriharto et al. | 340/825.49 |

OTHER PUBLICATIONS

Brochure, "Sure-Med Unit-Dose Center" 1996, Baxter Healthcare Corporation.
Brochure, "Sure-Med Modular Dispensing Center" 1995, Baxter Healthcare Corporation.

(Continued)

*Primary Examiner* — John Pauls
(74) *Attorney, Agent, or Firm* — Reising Ethington P.C.

(57) ABSTRACT

Methods, systems, and apparatuses to facilitate administering of medication.

24 Claims, 16 Drawing Sheets

(56) References Cited

OTHER PUBLICATIONS

Brochure, "Sure-Med Modular Expansion Cabinet" 1996, Baxter Healthcare Corporation.
Brochure, "Sure-Med Supply System" 1997, Baxter Healthcare Corporation.
Brochure, "PyxisStation, Providing Custom Solutions to Meet Diverse Needs" 1996, Pyxis Corporation.
Brochure, "Comprehensive Mobile Technology Solutions" 2004, Artromick International, Inc. Form A-075 Rev. 7/05.
Brochure, "Introducing the Latest Technology in Medication Cart Management" MMI Medcarts.
Brochure, "A Place for Everything" 1996, Artromick International, Medicart, LLC.
Brochure, "Artromick Medication Systems Worldwide" 1996, Artromick International, Medicart, LLC.
Brochure, "Good medicine made simple!" Envoy Automated Medication System.

* cited by examiner

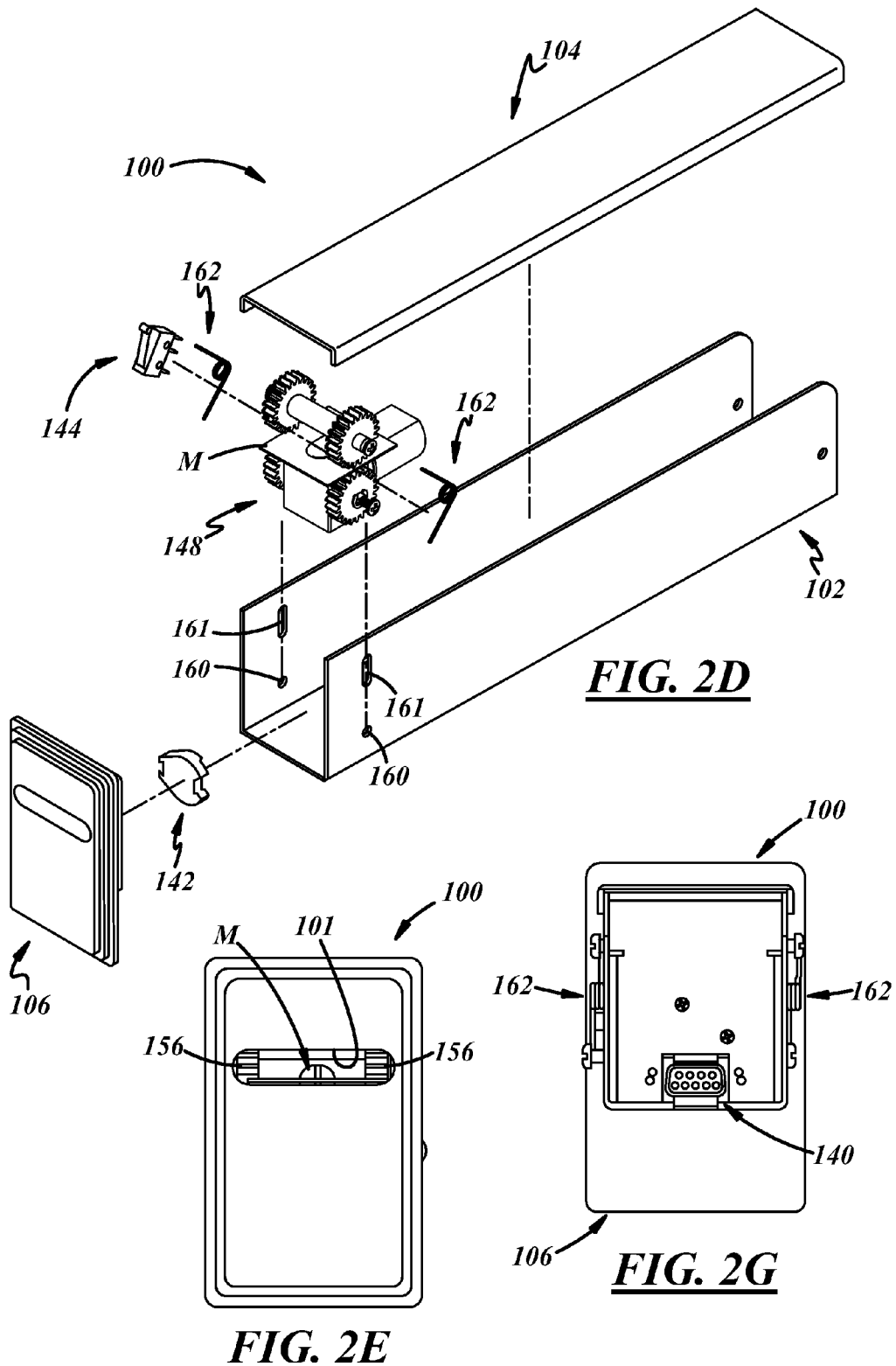

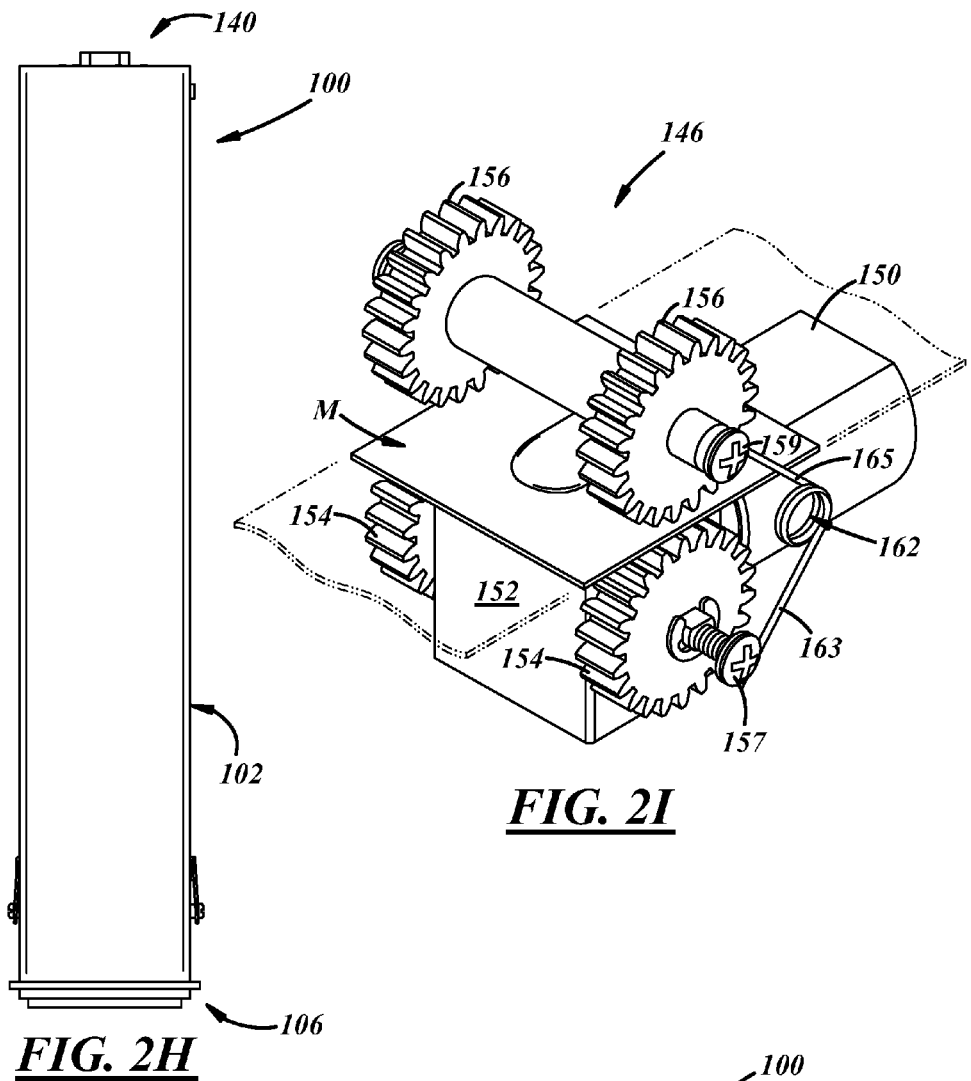
*FIG. 2I*
*FIG. 2H*
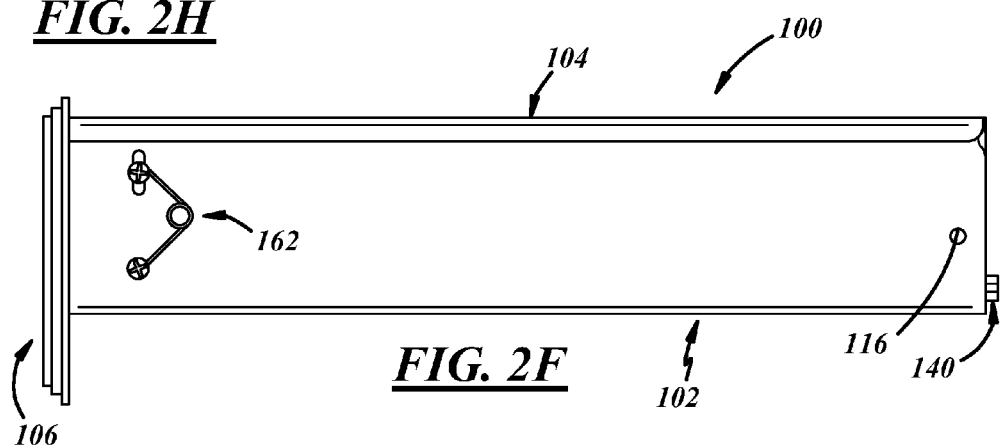
*FIG. 2F*

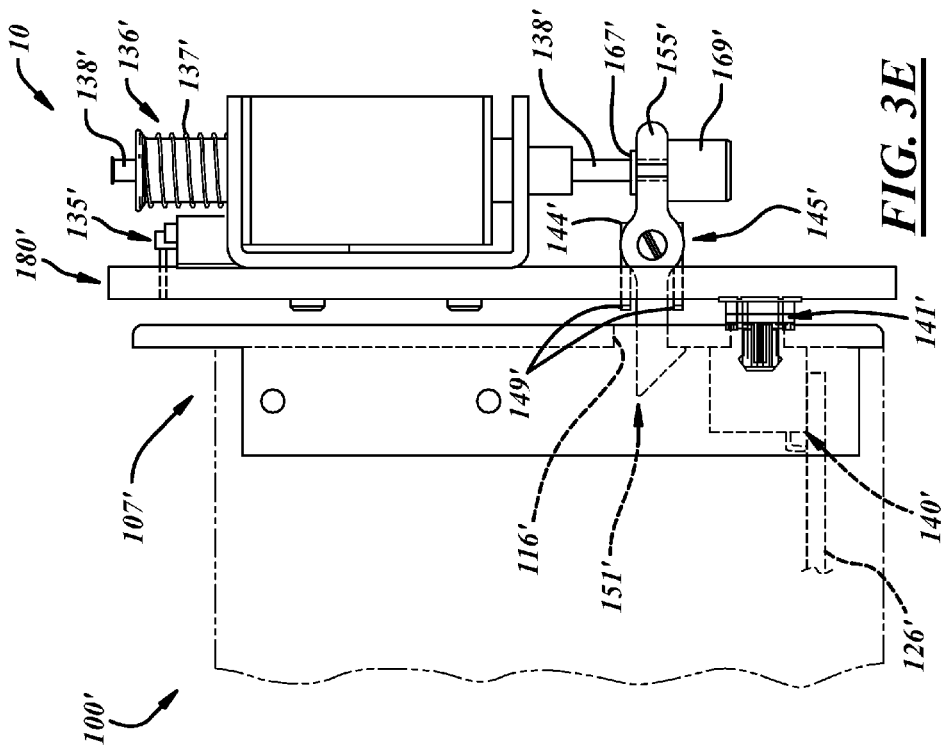
FIG. 3E
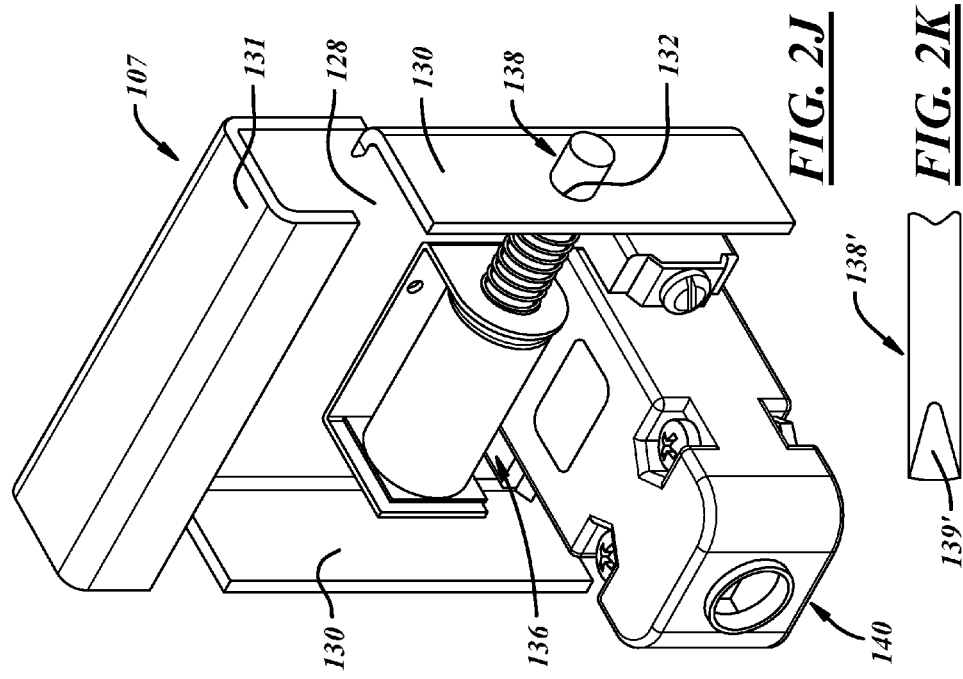
FIG. 2J
FIG. 2K

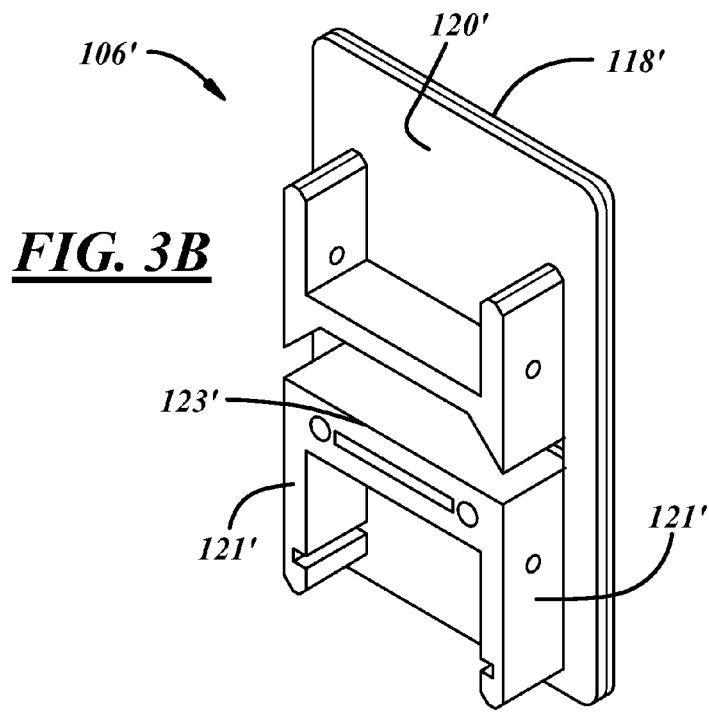
*FIG. 3B*
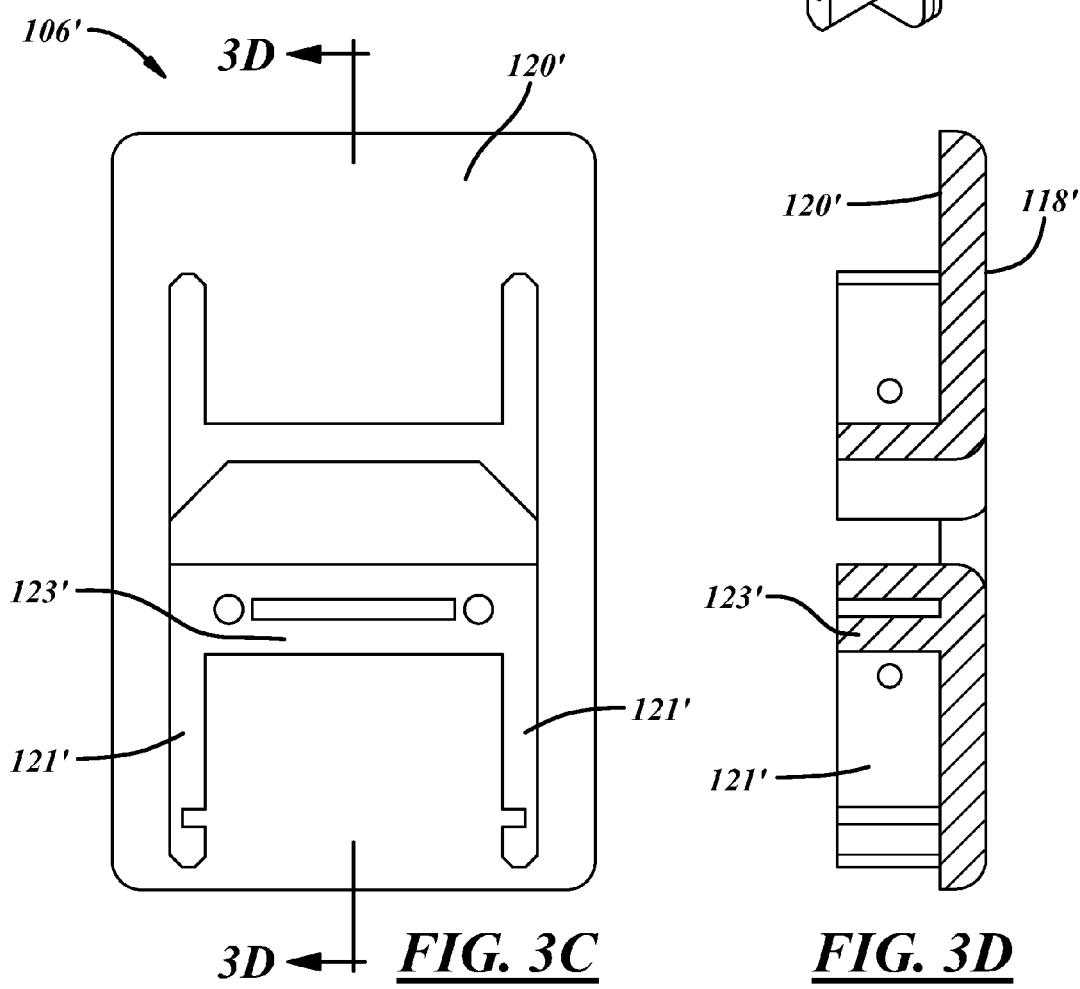
*FIG. 3C*
*FIG. 3D*

ADMINISTERING OF MEDICATION

CROSS-REFERENCE TO RELATED APPLICATION

This application claims the benefit of U.S. Provisional Application No. 61/110,321, filed Oct. 31, 2008, the content of which is incorporated herein by reference in its entirety.

TECHNICAL FIELD

The field to which the disclosure generally relates includes administering of medication.

BACKGROUND

In a typical inpatient setting, medication prescriptions are generated by a physician and dispensed by a pharmacist according to a dosing regimen (e.g. one pill twice daily or two pills twice daily). Also, computerized medication administering carts are frequently used in medical care facilities to administer medication to patients on a patient-by-patient basis. For example, such carts typically include a plurality of drawers or sections of drawers corresponding to a plurality of patients, wherein each drawer or drawer section is assigned to a particular patient and contains multiple doses of medication specifically prescribed for and assigned to the patient. Patients often leave the facility before finishing their assigned supplies of medication on the cart or the prescription may be terminated or changed and, thus, leftover medication may be discarded. In a hospital setting, medication typically is not discarded, but is usually recounted and replaced into a pharmacy inventory in a labor intensive process.

BRIEF SUMMARY

The present disclosure is directed to a medication administering apparatus that may be associated with a pharmacy, a medication administering cassette for the medication administering apparatus, a method of managing medication that may use the administering apparatus, and a medication administering system.

BRIEF DESCRIPTION OF THE DRAWINGS

Exemplary embodiments of the invention will become more fully understood from the detailed description and the accompanying drawings, wherein:

FIG. 2D is an exploded perspective view of the cassette of FIG. 2A;

FIG. 2E is a front view of the cassette of FIG. 2A;

FIG. 2F is a right side view of the cassette of FIG. 2A;

FIG. 2G is a rear view of the cassette of FIG. 2A;

FIG. 2H is a top view of the cassette of FIG. 2A;

FIG. 2I is a perspective view of a material handling apparatus of the cassette of FIG. 2A;

FIG. 2J is a perspective view of an exemplary embodiment of a locking apparatus and electrical connector of the cassette of FIG. 2A;

FIG. 2K is a fragmentary view of an exemplary embodiment of a shot pin for the locking apparatus of FIG. 2J;

FIG. 3B is a rear perspective view of an exemplary embodiment of a front cover of the cassette of FIG. 3A;

FIG. 3C is a rear plan view of the front cover of FIG. 3B;

FIG. 3D is a sectional view of the front cover of FIG. 3B, taken along line 3D-3D of FIG. 3C;

FIG. 3E is a fragmentary side view of another exemplary embodiment of a locking apparatus and electrical connector for the cassettes of FIGS. 2A and/or 3A and the computerized medication administering apparatus of FIG. 1;

DETAILED DESCRIPTION OF EXEMPLARY EMBODIMENTS

The following description of the embodiment(s) is merely exemplary (illustrative) in nature and is in no way intended to limit the invention, its application, or uses.

Figure 1:
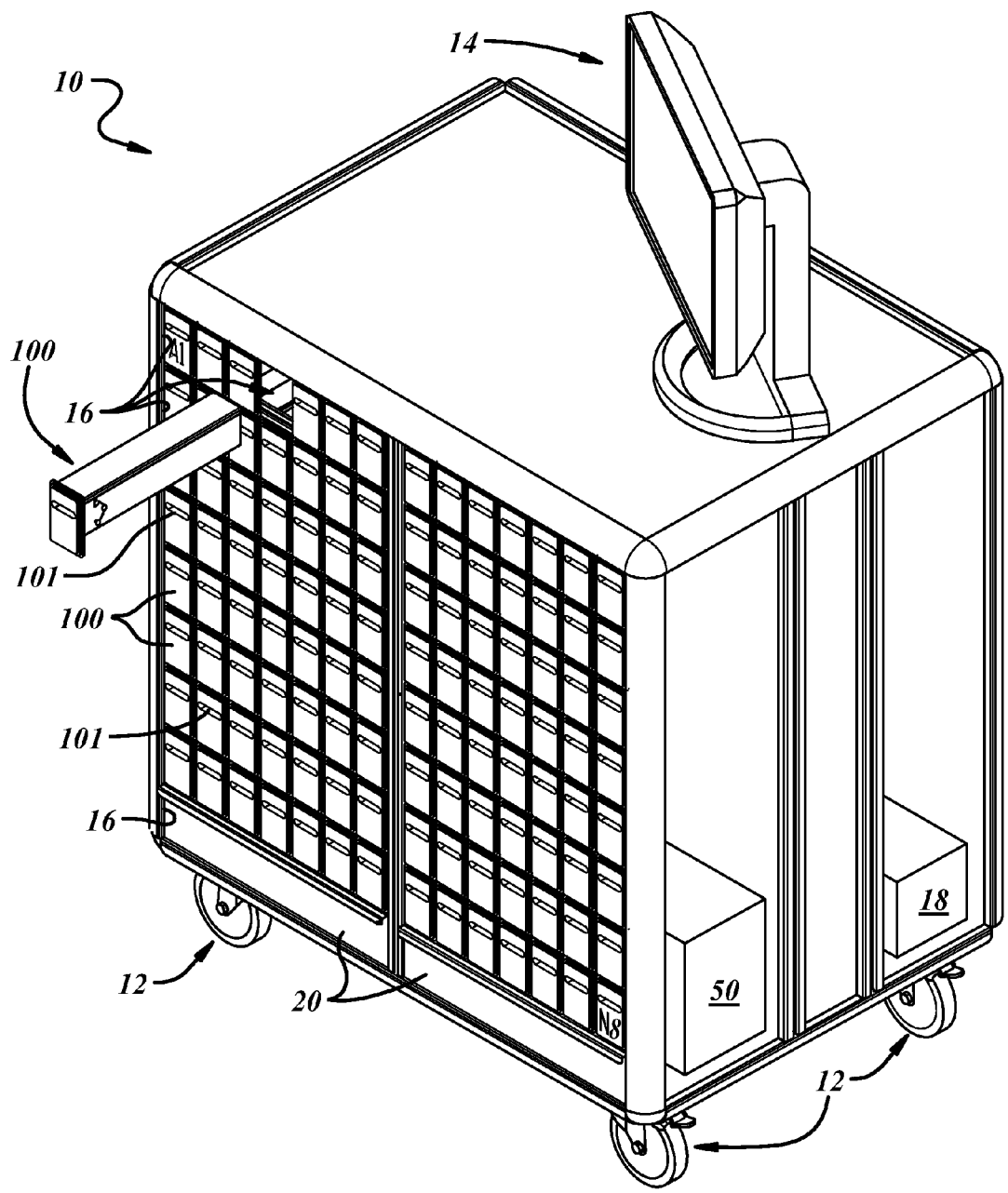
FIG. 1 is a perspective view of a computerized medication administering apparatus according to one exemplary embodiment, and illustrating a cassette exploded out of a corresponding compartment.

FIGS. 1-4 illustrate an apparatus according to exemplary embodiments. As shown in FIG. 1, a computerized medication administering apparatus 10, which, according to one embodiment, may include a mobile cart as shown. For example, the disclosure of U.S. Pat. No. 6,175,779 is incorporated herein by reference in its entirety. A plurality of wheels 12 may be mounted to the apparatus 10 to permit transport of the apparatus 10 from room to room by a medication administering attendant while making patient rounds. In another embodiment, the apparatus 10 may be stationary, for example, built into a workstation, cabinet, desk, or the like in any suitable facility. In any event, the apparatus 10 may be located remotely from a pharmacy with which the apparatus 10 may be associated. For example, the apparatus 10 may be owned or leased by a pharmacy. As used herein, the terminology administering attendant includes a nurse, nursing assistant, physician, physician's assistant, or any other suitable individual for administering medication. As also used herein, the terms administer and administrate are used interchangeably and include providing medication specifically to a patient in contrast to the term dispensing, which includes making medication generally available to a patient for administering to that patient.

The apparatus 10 may include a touch screen monitor 14 mounted on the apparatus 10 for easy access and view by the attendant. The touch screen monitor 14 may be further equipped with a conventional mouse or keyboard or replaced with a conventional monitor equipped with a conventional mouse or keyboard. The apparatus 10 may include a housing (either for the mobile cart or the stationary apparatus embodiments) including a plurality of compartments 16 for receiving administering devices or cassettes 100 and conventional storage drawers 20. The conventional storage drawers 20 may be used to store bandages and other types of medical supplies as well as other medications that cannot be easily packaged such as medications in liquid form, creams, lotions, powders, etc. for administering to a patient. For security purposes, such drawers 20 may be locked. The plurality of compartments 16 may house a computer 50 and one or more batteries 18 for powering the computer 50, cassettes 100, EEPROM, release mechanisms, and any other powered elements of the apparatus 10. Of course, the apparatus 10 may be supplied with power in any other suitable manner, including AC utility or generator power, or the like.

In one embodiment, shown in FIG. 1, the cassettes 100 may be loaded and unloaded from the cart or apparatus housing and used for receiving, storing, and/or administering patient-unassigned medication. As used herein, the term medication includes prescription medication, vitamins, supplements, over the counter medication, and/or the like. As also used herein, the term patient-unassigned means that particular doses of medication have not yet been assigned to any particular patient(s), but that eventually may become so assigned. In other words, although a type of medication generally may be approved for administering to a particular patient, the medication is not assigned to the particular patient until actually removed from the cassette(s) 100 for administration to the particular patient.

The cassettes 100 may be arranged in the apparatus 10 in an array, as shown, or in any other suitable arrangement. In an array, the cassettes 100 may be identified by column and row. For example, as shown in FIG. 1, there are eight rows and fourteen columns that may be identified alphanumerically. For instance, the rows may be identified as rows A through N and the columns may be identified as columns one through eight.

In any event, each cassette 100 corresponds to a particular medication. For instance, a given cassette, say in location A1 of the apparatus 10, may receive, store, and administer a particular type or brand of analgesic, while another device, say N14, may receive, store, and administer a specific type or brand of antihistamine. One particular medication may correspond to more than one cassette 100 on the apparatus 10. For example, a medication may be so popular that several cassettes 100 may be required to receive, store, and administer that particular popular medication. Accordingly, the cassettes 100 of the administering apparatus 10 need not be organized by patient and, thus, each cassette 100 need not correspond to a particular patient. Rather, the apparatus 10 is organized by medication, wherein the cassettes 100 correspond to particular medications.

Figure 2A:
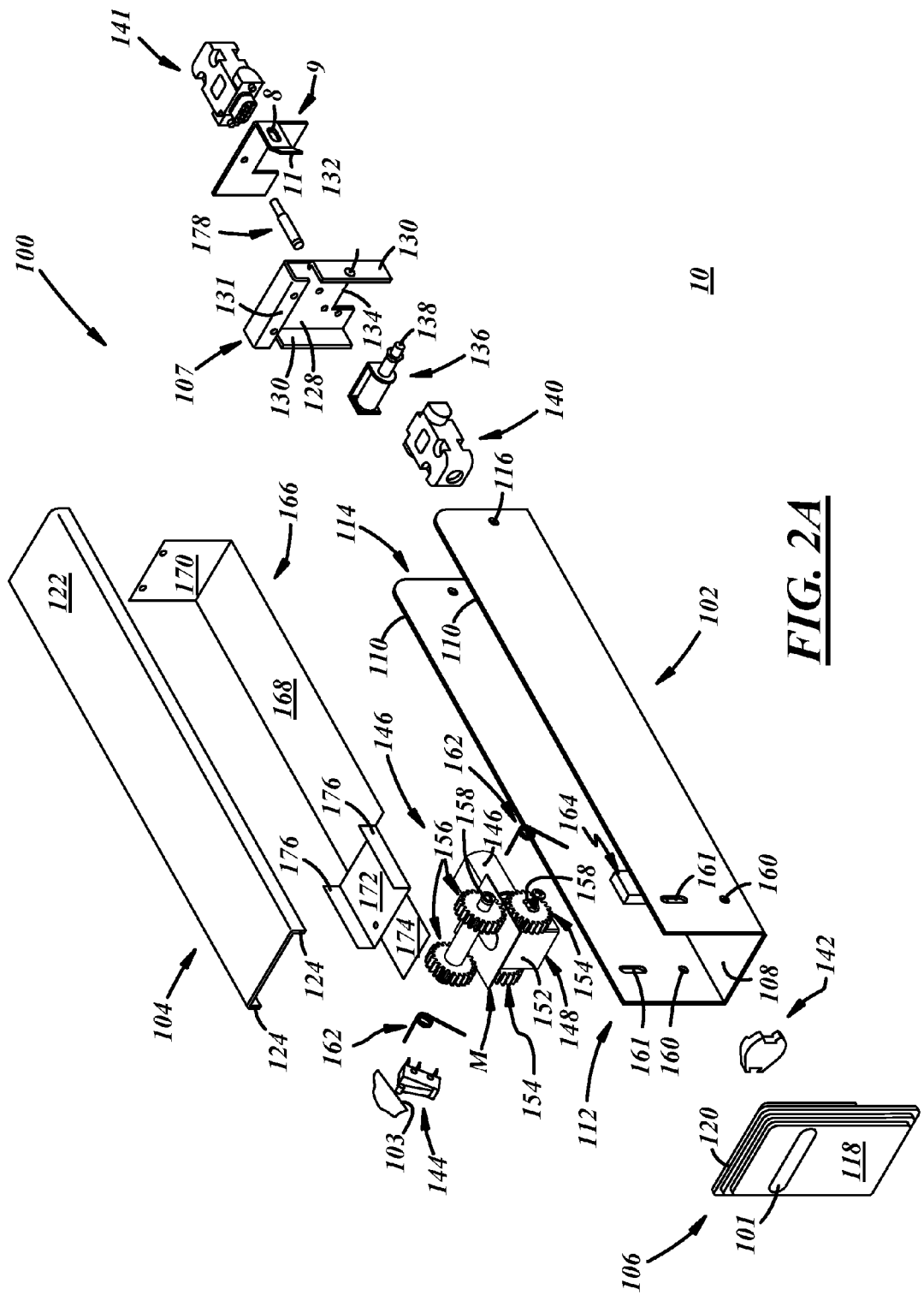
FIG. 2A is an exploded perspective view of an exemplary embodiment of the cassette of the computerized medication administering apparatus of FIG. 1.

In a particular example illustrated in FIG. 2A, the exemplary cassette 100 includes a housing that may be comprised of a main body 102 to provide support for other portions of the cassette 100, a top cover 104 that covers the main body 102, and a front cover 106 that frontally covers the main body 102 and includes an outlet 101, for example a slit, through which medication may be conveyed, and a rear cover or bracket 107 that covers a rearward end of the main body 102. The main body 102 includes a base 108, sides 110 extending from the base 108, a front 112 to which the front cover 106 is coupled in any suitable manner, and a rear 114. One or both of the sides 110 includes a locking aperture 116 therethrough. The front cover 106 includes a front portion 118, a rear portion 120 coupled to the main body 102, and the outlet 101 extending therethrough. The top cover 104 includes a top base 122 and flanges 124 extending therefrom, wherein the top cover 104 is coupled to the main body 102 in any suitable manner. For example, the sides 110 of the main body 102 may be frictionally engaged to the flanges 124 of the top cover.

The bracket 107 may include a base 128, flanges 130 extending from the base 128 for coupling to the sides 110 of the main body 102 of the housing, and an upper lip 131. One or both of the flanges 130 may include a locking aperture 132 therethrough. The bracket 107 may include a connector passage 134 in the base 128.

The apparatus 10 may also include an electromechanical latch to selectively couple the cassette 100 to the cart or apparatus housing and including a locking device 136, for example, a solenoid that may be coupled to the bracket 107 in any suitable manner, for example, with fasteners or the like. The electromechanical actuator 136 may include a shot pin 138 that is biased to a normally extended position, for example by a spring. The pin 138 extends through the locking aperture 132 of the bracket 107, and through the locking aperture 116 of the body 102 when the bracket 107 is assembled to the body 102. When the housing is pushed into the compartment of the apparatus 10, an angled front flange 11 of a structural member 9 of the cart or apparatus housing, for example, a bracket or the like, engages the pin 138 so as to retract the pin 138 against the bias force of the spring and allow the cassette 100 to advance past the angled front flange 11 until the pin 138 snaps into a locking aperture 8 of the structural member 9 of the cart when the pin 138 and the aperture 8 align.

In the embodiment shown in FIG. 2K, the end of a pin 138' may be provided with an angled or cam surface 139'. Therefore, if the bracket 9 is provided with a straight edge instead of the angled front flange 11, the straight edge may engage the cam surface 139' of the end of the pin 138' so as to retract the pin 138' against the bias force of the spring and allow the cassette 100 to advance past the straight edge of the bracket until the pin 138' snaps into a locking aperture 8 of the structural member 9 of the cart or housing when the pin 138' and the aperture 8 align. This action locks the cassette 100 to the apparatus 10.

Thus, in one embodiment, the administering apparatus 10 includes locking cassettes. The cassette locking may be accomplished using the spring force of the actuator 136 to advance the pin 138, 138' into the locking aperture 8 of the cart or housing, and unlocking may be accomplished by energizing the solenoid to retract the shot pin 138, 138'. The cassette 100 will remain in the locked state until the signal is sent from the computer 50 of the administering apparatus 10 to the actuator 136 to unlock the cassette 100.

The cassette 100 also includes an electrical connector 140 that may be coupled to the bracket 107 in any suitable manner and that may at least partially pass through the connector passage 134 of the bracket 107. The connector 140 engages an electrical connector 141 of the apparatus 10 that corresponds to the compartment 16 in which the cassette 100 is disposed. The connector 141 may be coupled to a backplane (not shown) of the apparatus 10 that, in turn, may be coupled in any suitable manner to the computer 50. The computer 50 is in communication with the connectors 141 and is programmed in accord with the array of compartments 16. Accordingly, the location of the cassettes in the compartments can be communicated to and stored in the computer 50 in any suitable manner. The connectors 140, 141 may be, for example, blind hole low friction 15-pin connectors. Of course, although not shown in the drawings, any suitable power and data wires or the like may be coupled between the actuator 136 and connector 141 and corresponding portions of the apparatus 10, such as a power supply, computer, and/or the like. The low friction connectors 140, 141 are constructed so that the cassette connector 140 is inherently guided into the mating cart connector 141 with little to no effort, for example, 0.1 to 0.4 lbs of force and, more specifically about 0.2 lbs of force. Also, the low friction connectors 140, 141 are constructed so that the cassette connector 140 is easily disengaged from the mating cart connector 141 when the cassette 100 is unlocked from the cart. In fact, the cassette spring pressure is sufficient to automatically at least partially advance the cassette 100 out of its corresponding compartment 16 upon being unlocked.

The cassette 100 also includes a memory device 142 disposed at the front end 112 of the main body 102 and that may be coupled to the rear 120 of the front cover 106 in any suitable manner. The device 142 may be an EPROM or EEPROM device, for example, an I-BUTTON brand device, or the like.

The cassette 100 further includes a switch 144 that may be coupled to the housing in any suitable manner and that may cooperate with any suitable portion of the apparatus 10 as the cassette 100 is pulled out of the compartment 16 or fully closed into the compartment 16. For example, the switch 144 may be coupled to the rear 120 of the front cover 106 and may cooperate with a front inside edge 13 of the cart or housing of the apparatus 10. The switch 144 may indicate a status of the cassette 100, for example, an open and/or closed position.

The cassette 100 additionally includes a material handling apparatus or material handler 146 to move medication M out of the housing. For example, the material handler 146 may feed or convey a strip of packaged medication M out of the housing and through the outlet 101. Although only one medication unit or dose is illustrated, the strip may include a plurality of medication units or doses and may be rolled or folded back onto itself in a compact manner within the housing, or may be wound on a spool or reel, or the like. As used herein, the term medication may include anything for topical treatment or internal care of patients and in any form, including but not limited to solids, liquids, powders, gels, creams, lotions, ointments, syringes, sprays or sprayers, bandages, gauze, or any other supplies. According to a liquid form embodiment, the strip of the medication M may be produced according to a FLUIDOSE brand unit dose packaging available from Medical Packaging Inc. (MPI) of Ringoes, N.J. or according to any other strip type of packaging available from MPI or any other suitable source.

More particularly, the apparatus 146 may include a powertrain 148 including a prime mover or motor 150 and a drivetrain coupled to the motor 150 in any suitable manner and that may include a transmission or gearbox 152 having an input coupled to the motor 150 and drive elements 154 coupled to one or more output shafts of the gearbox 152 to drive the strip of medication M. The drive elements 154 may be toothed wheels or gears, or other meshing elements, or any other suitable drive elements. Accordingly, an attendant may use the computer 50 to administer medication, for example, by accessing a data file or record for a patient to whom the medication is to be administered and instructing the system 50 to send an appropriate signal to the motor 150 to advance and convey a dose of the medication out of the cassette 100. The attendant may instruct the system 50 in any suitable manner, for example by keying in commands with a keyboard, selecting an option with a pointing device, for example, a mouse, touchscreen, or the like.

Although not shown, the motor 150 may include a drive worm on an output shaft that is coupled to a driven worm gear of the gearbox 152. The drive worm may drive the driven worm gear but the opposite is not true. This provides an additional locking mechanism for the cassette 100, because such unidirectional or one-way operation of the powertrain prevents someone from pulling the medication strip through the outlet 101. Once administering of a unit is complete, and the powertrain stops, the transmission or drivetrain locks. This may prevent tampering with the apparatus 10. The drive/driven worm arrangement is just one exemplary one-way powertrain configuration for the material handler 146 and any other suitable one-way configurations also or instead may be used.

Figure 2B:
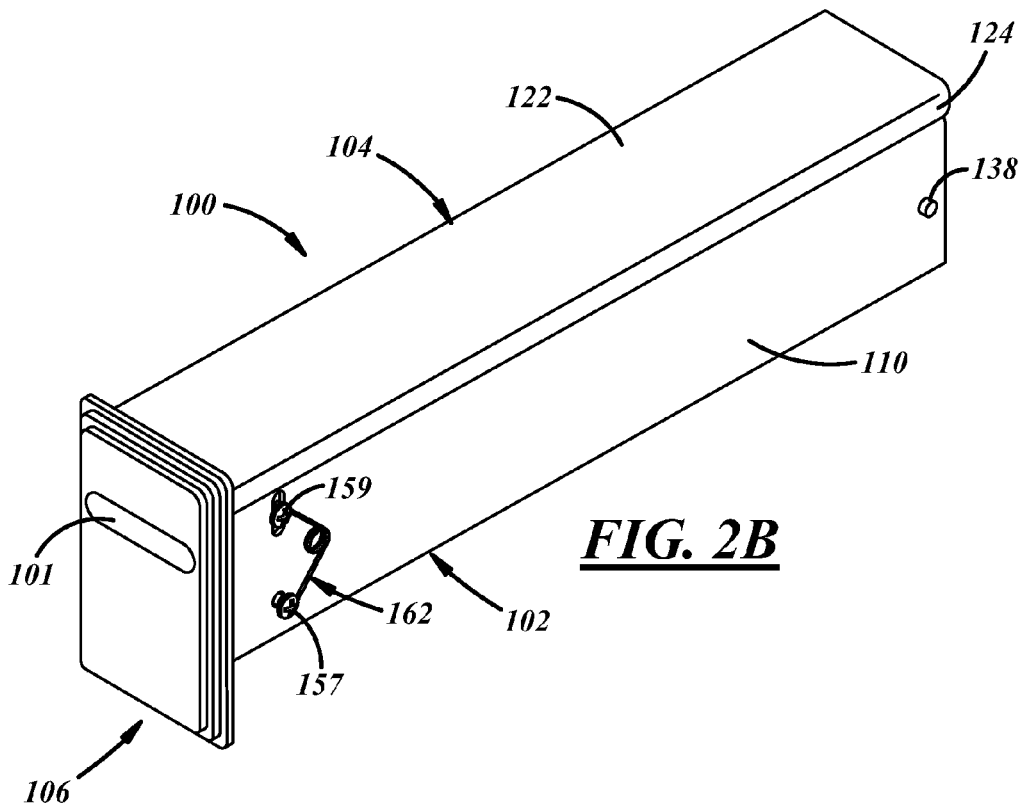
FIG. 2B is a perspective right side view of the cassette of FIG. 2A.
Figure 2C:
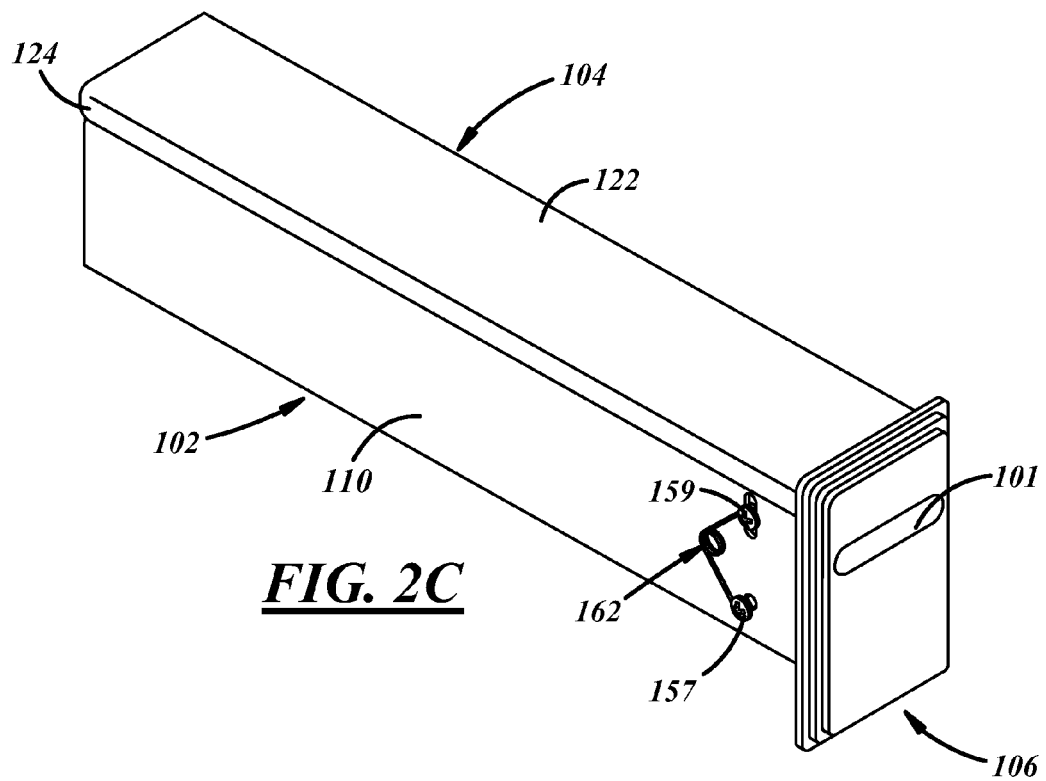
FIG. 2C is a perspective left side view of the cassette of FIG. 2A.

The material handler 146 may also include driven elements 156 and an axle on a side of the medication M opposite that of the drive elements 154. The driven elements 156 may be toothed wheels or gears, or other meshing elements, or any other suitable driven elements. The powertrain 148 may be coupled to the housing in any suitable manner, for example, the elements 154, 156 may be mounted on shafts or hubs 158 that may be supported by corresponding apertures 160, 161 in the sides 110 of the main body 102. The upper apertures 161 may be slots to accommodate up and down movement of the driven elements 156. As shown in FIG. 2B, screws 157, 159 may be coupled to the hubs 158 through the walls 110 of the body 102 to retain the material handler 146 in a desired position within the housing. The material handler 146 may further include guide springs 162 that may be operably coupled to the hub or shaft 158 of the driven elements 156, for example, by engaging the screws 157, 159 outboard of the walls 110 of the body 102. As shown in FIG. 2I, the springs 162 include lower arms 163 that may terminate in hooks, loops, or the like located behind the heads of the lower screws 157 to couple the springs 162 thereto, and upper arms 165 that may terminate in hooks, loops, or the like located behind the heads of the upper screws 159 to coupled the springs 162 thereto. Accordingly, the springs 162 are constructed and arranged to bias the driven elements 156 in a direction away from the drive elements 154 so as to release the medication M when the top cover 104 is lifted. When the top cover 104 is pressed down on the body 102 the base 122 presses down on the driven elements 156, wherein the medication M is gripped between the driven elements 156 and the drive elements 154.

The material handler 146 additionally may include a medication counting device or counter 164 that may be coupled in any suitable manner to the housing so as to count the quantity of medication doses that passes through the outlet 101. Accordingly, the apparatus may administer medication on a unit dose, unit-of-use, or dose-by-dose basis. The counter 164 may be coupled to one or both of the sides 110 and may cooperate with one or both of the drive elements 154 and/or the medication packaging to count each dose of medication. For example, the counter 164 may be a mechanical switch with an armature in contact with the drive elements 154 to count a passing of each of several teeth. In another example, the counter 164 may be an optical sensor to count a passing of each tooth or spoke or the like of the drive element 154. In a further example, the counter 164 may be a switch, sensor, or the like that may directly sense separable portions of the packaged medication strip.

The cassette 100 may also include a protective cover 166 to cover the wires or a circuit board (not shown) and a portion of the material handler 146, and/or to guide the medication M. The cover 166 may include a base 168, which may be generally planar, and a rear flange 170 extending rearwardly from the base 168 that may be fastened or otherwise coupled to the lip 131 of the bracket 107. The cover 166 may also include a front flange 172 extending forwardly from the base 168 to cover the motor 150 and a tongue 174 extending forwardly from the front flange 172 to cover the gearbox 152. The front flange 172 may include guides 176 disposed on lateral sides thereof. The guides 176 and the tongue 174 may assist with guiding the medication M through the apparatus 146.

Finally, a biasing member 178 may be carried by any suitable portion of the cart, for example, the bracket 9, to bias the cassette 100 toward an opened position. In one example, the biasing member 178 may include a spring-loaded pin device that may be coupled to the bracket 9 with a portion of the pin device extending between the brackets 9, 107. Accordingly, when the cassette 100 is fully inserted into the compartment 16 of the cart and the actuator 136 locks the cassette 100 to the cart, the biasing member 178 is loaded. Therefore, when the actuator 136 is energized to unlock the cassette 100 from the cart, the bias force of the biasing member 178 acts on the bracket 107 of the cassette 100 to push the cassette 100 in an outward direction from the cart. Accordingly, the cassette 100 may "pop open" when the cassette 100 is unlocked from the cart.

The pin 138 extends through the locking aperture 132 of the bracket 107, and through the locking aperture 116 of the body 102 when the bracket 107 is assembled to the body 102. When the housing is pushed into the compartment of the apparatus 10, an angled front flange 11 of a structural member 9 of the cart, for example, a bracket or the like, engages the pin 138 so as to retract the pin 138 against the bias force of the spring and allow the cassette 100 to advance past the angled front flange 11 until the pin 138 snaps into a locking aperture 8 of the structural member 9 of the cart when the pin 138 and the aperture 8 align.

FIGS. 3A-3G illustrate another exemplary embodiment of a cassette 100' that may be used with the apparatus 10 of FIG. 1. This embodiment is similar in many respects to the embodiment of FIGS. 2A-2K and like numerals between the embodiments generally designate like or corresponding elements throughout the several views of the drawing figures. Additionally, the descriptions of the embodiments are incorporated by reference into one another and the common subject matter generally may not be repeated here.

Figure 3A:
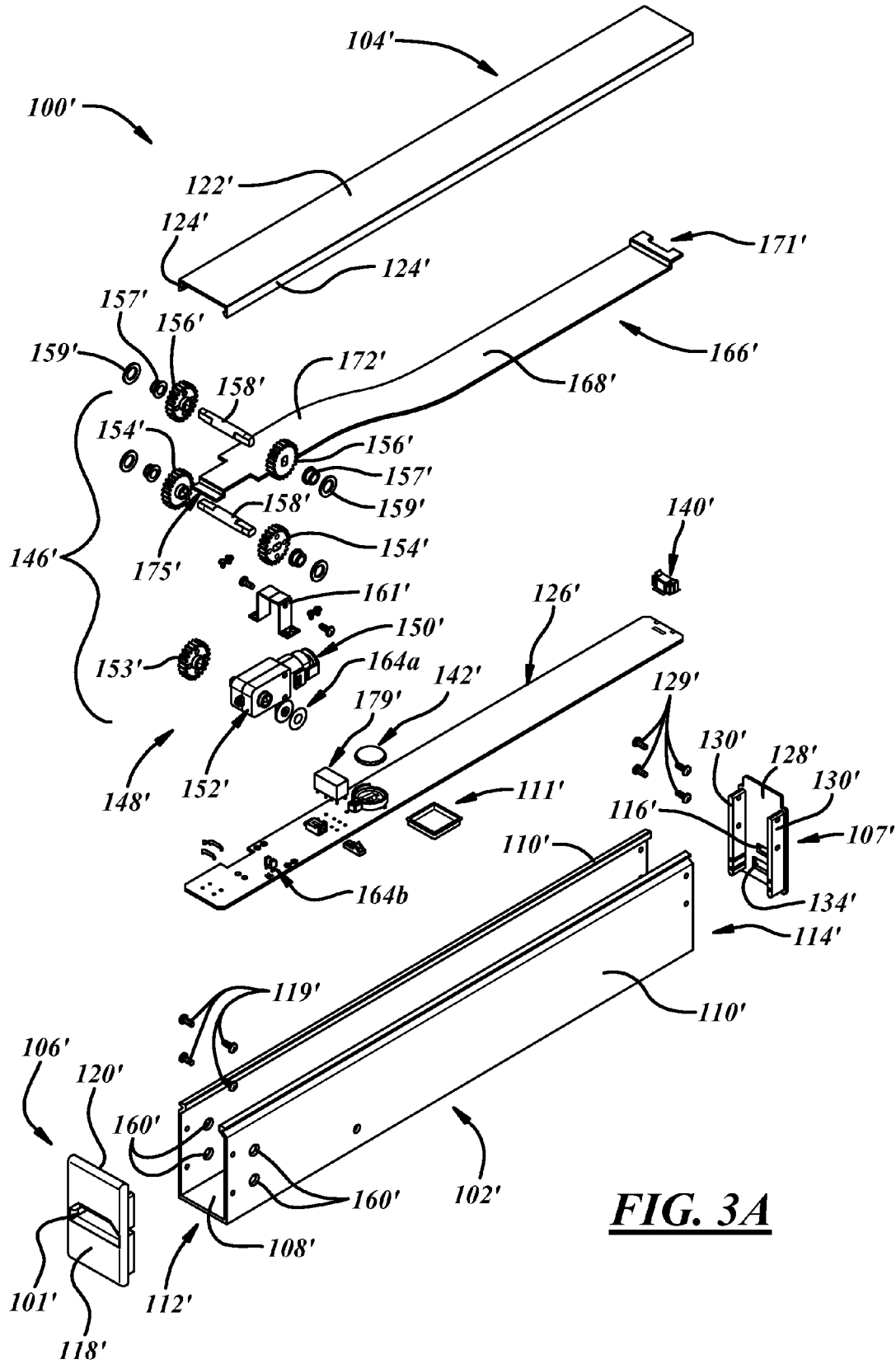
FIG. 3A is an exploded perspective view of another exemplary embodiment of the cassette of the computerized medication administering apparatus of FIG. 1.
Figure 3G:
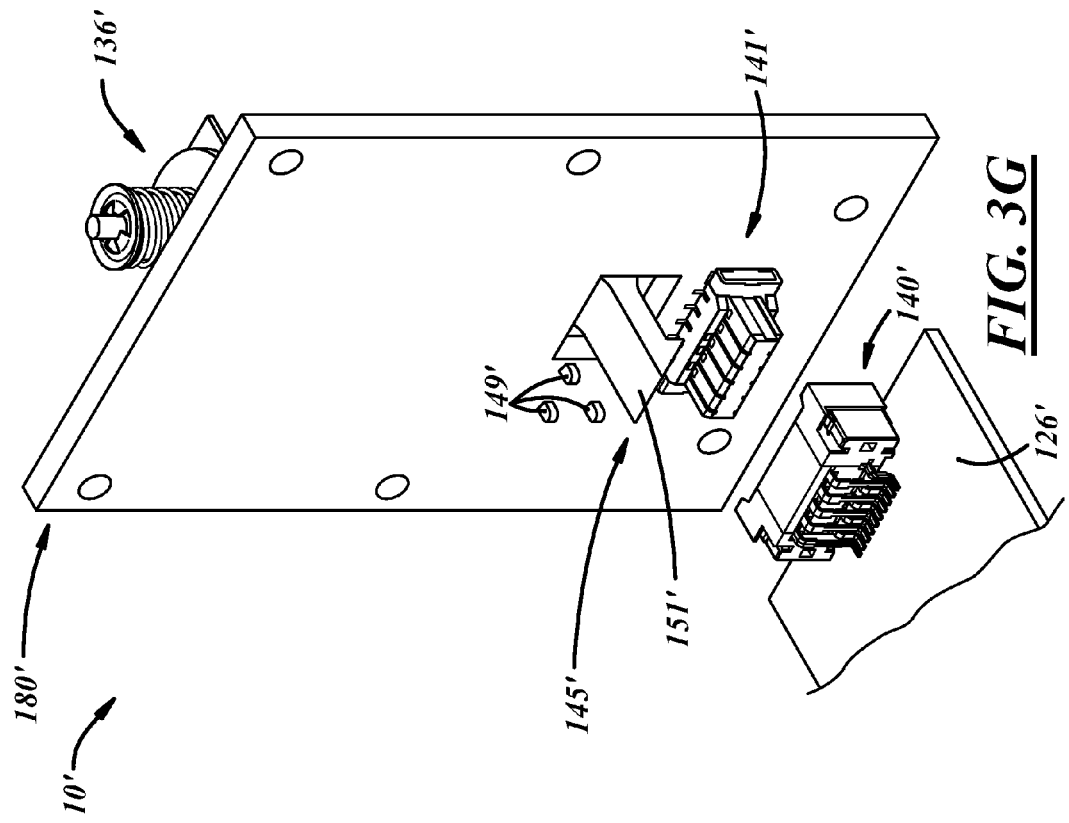
FIG. 3G is a fragmentary perspective front view of the locking apparatus portion of FIGS. 3E and 3F and the electrical connector portion of FIG. 3E.
Figure 3F:
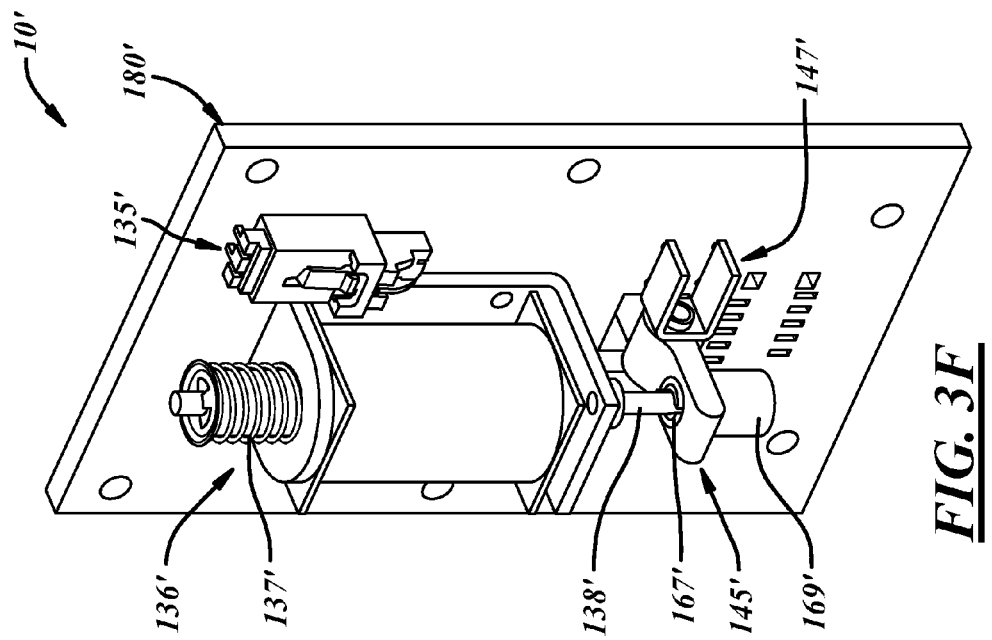
FIG. 3F is a fragmentary perspective rear view of the locking apparatus portion shown in FIG. 3E.

In a particular example illustrated in FIG. 3A, the exemplary cassette 100' includes a housing that may be comprised of a main body 102' to provide support for other portions of the cassette 100', a top cover 104' that covers the main body 102', and a front cover 106' that frontally covers the main body 102' and includes an outlet 101' through which medication may be conveyed, and a rear cover 107' that covers a rearward end of the main body 102'. The top cover 104' may be identifiable as part number C1.5LG6 available from PANDUIT of Tinley Park, Ill. The top cover 104' also may be custom molded, for example, using ALUMILITE brand molds and techniques.

The main body 102' includes a base 108', sides 110' extending from the base 108', a front 112' to which the front cover 106' may be coupled in any suitable manner, and a rear 114' to which the rear cover 107' may be coupled in any suitable manner. The main body 102' may be a drawer base identifiable by part number FS1.5x3LG6NM available from PANDUIT of Tinley Park, Ill. The main body 102' also may be custom molded, for example, using ALUMILITE brand molds and techniques.

Referring also to FIGS. 3B and 3C, the front cover 106' includes a front portion 118', a rear portion 120' coupled to the main body 102', and the outlet 101' extending therethrough. The front cover 106' may include flanges 121' extending from the rear portion 120' for coupling to the sides 110' of the main body 102' in any suitable manner for example via fasteners 119'. The front cover 106' also may include a cross-member 123' extending from the rear portion 120' and between the flanges 121'.

Referring to FIG. 3A, the top cover 104' includes a top base 122' and flanges 124' extending therefrom, wherein the top cover 104' is coupled to the main body 102' in any suitable manner. For example, the sides 110' of the main body 102' may be frictionally slidably interengaged to the flanges 124' of the top cover 104'.

The rear cover 107' may include a base 128', and flanges 130' extending from the base 128' for coupling to the sides 110' of the main body 102' of the housing in any suitable manner for example via fasteners 129'. The bracket 107 may include a locking aperture 116' and a connector passage 134' extending through the base 128'.

The cassette 100' further may include a circuit board 126' having forward and rearward ends, which may be carried or engaged in corresponding slots in the flanges 121', 130' of the front and rear covers 106', 107' and supported by the base 108' of the body 102' by a bumper 111'. The bumper 111' may be a 1036 bumper available from Action Fabricators of Grand Rapids, Mich. Those of ordinary skill in the art will recognize that the design of the board 126' may be application specific, and may be purchased from any suitable source, for example, K&F Electronics of Fraser, Mich.

The cassette 100' also may include an electrical connector 140' that may be coupled to the circuit board 126' in any suitable manner and that may at least partially pass through the connector passage 134' of the rear cover 107'. The connector 140' may be identifiable as part number BTFW10R-3RSTAE1LF available from FCI of Versailles Codex, France. The cassette 100' also may include a memory device 142' coupled to the circuit board 126' for example via a memory device mount 143'. The device 142 may be a MAXIM brand memory chip, for example, with model number DS1972-F3#, and the mount 143' may be KEYSTONE brand mount, for example, with model number 101.

The cassette 100' additionally may include a material handling apparatus or material handler 146' to move medication out of the housing and through the outlet 101' of the front cover 106'. More particularly, the apparatus 146' may include a powertrain 148' including a prime mover or motor 150' and a drivetrain coupled to the motor 150' in any suitable manner and that may include a transmission or gearbox 152' having an input coupled to the motor 150'. The powertrain 148' may be identifiable as part number GM3 available from SOLARBOTICS of Calgary, Canada.

The apparatus 146' also may include drive elements 154' carried on an axle and coupled to one or more output elements 153' of the gearbox 152' to drive the strip of medication (not shown). The drive elements 154' may be toothed wheels or gears, or other meshing elements, or any other suitable drive elements. The material handler 146' may also include driven elements 156' carried on an axle on a side of the medication opposite that of the drive elements 154'. The driven elements 156' may be toothed wheels or gears, or other meshing elements, or any other suitable driven elements.

The powertrain 148' may be coupled to the housing in any suitable manner, for example, the elements 154', 156' may be mounted on axles 158' that may be supported by corresponding apertures 160' in the sides 110' of the main body 102'. Bushings 157' may be coupled to the axles 158' through the walls 110' of the body 102' with washers 159' between the bushings 157' and the walls 110'. The bushings 157' may be identifiable as part numbers 318C available from WCL of Industry, Calif. The material handler 146' may further include a bracket 161' to couple the powertrain 148' to the circuit board 126'.

The material handler 146' additionally may include a medication counting device or counter 164' that may be coupled in any suitable manner to the housing so as to count the quantity of medication doses that passes through the outlet 101'. The counter 164' may be an encoder that may include, for example, an encoder wheel and sticker 164a coupled to an output shaft of the gearbox 152' and an encoder sensor 164b coupled to the circuit board 126' to count alternating portions of the encoder wheel and sticker 164a. The encoder sensor 164b may be identifiable as part number EE-SX1106 available from OMRON of Kyoto, Japan, and the encoder sticker may be identifiable as part number 2923 and available from SIGNARAMA. The sticker may include alternating black and white segments, for example, 18 black and 18 white segments. As shown, the cassette 100' may include any suitable resistors as voltage dividers to reduce voltage to the encoder sensor 164b.

The cassette 100' additionally may include a relay 179' coupled to the board 126' and in communication with the powertrain motor 150'. The relay 179' may have two functions; when the relay 179' is energized it may power the motor 150' for feeding the packaged medication out of the cassette 100', and when the relay 179' is deenergized, it may act as a brake to keep someone from pulling the packaged medication out of the cassette 100'. The relay 179' may be a model number G5V-2-DC12 available from OMRON.

The cassette 100' may also include a protective cover 166' to cover the circuit board 126' and a portion of the material handler 146', and/or to guide the medication. The cover 166' may include a base 168', which may be generally planar, and a rear end 171' extending rearwardly from the base 168' that may be engaged in slots in the flanges 130' of the rear cover 107'. The cover 166' may also include a raised portion 173' extending forwardly from the base 168' to cover the motor 150' and the gearbox 152'. The cover 166' further may include a front end 175' extending forwardly from the base 168' that may be engaged in slots of the flanges of the front cover 106'. The cover 166' may assist with guiding the medication through the apparatus 146' and to the outlet of the front cover 106'. Those of ordinary skill in the art will recognize that the design of the cover 166' will be application specific, and may be created, for example, using ALUMILITE brand molds and techniques. The cover 166' may be composed of, for example, a polymeric material, for instance, polystyrene.

FIG. 3E illustrates a fragmentary side view of another embodiment of an electrical connecting and locking portion of a medication dispensing apparatus 10' similar to that of FIG. 1. This portion includes a rear cover 107' that may be used with the cassette 100' (shown in phantom), a backplane 180' that may be coupled in any suitable manner to internal framework of the housing of the apparatus 10', and a cassette locking apparatus coupled to the backplane 180' for cooperation with the rear cover 107' of the cassette 100' to selectively couple the cassette to the cart of the apparatus 10'.

The cassette electrical connecting portion includes an electrical connector 140' that may be coupled to and carried by an inside top surface of the circuit board 126' in any suitable manner, for example, by soldered pins. In turn, the circuit board 126' may be carried by the housing of the cassette (not separately shown). The apparatus 10' also includes an electrical connector 141' that may be coupled to the backplane 180' in any suitable manner, for example, by soldered pins. The connector 141' may be the counterpart connector for the cassette connector 140' and, for example, also may be from FCI of Versailles Codex, France. In any event, the connectors 140' and 141' are coupled to their respective supports such that they align and engage with one another. The connectors 140', 141' may be 10 pin connectors, and one or both may incorporate a floating insertion feature that allows a male end of the connector(s) to float horizontally and vertically making insertion easier.

The backplane 180' may include one or more circuit boards operatively coupled to a computer (not separately shown) of the apparatus 10' in any suitable manner. The backplane 180' may be fastened to any suitable structural members or framework of the housing of the apparatus 10'. Although not shown, any suitable hard stops may be provided between the cassette 100' and the framework of the apparatus housing to prevent the cassette 100' from damaging the backplane 180', for example, in the event that the cassette 100 is slammed to its closed position.

The locking portion may include an electromechanical actuator 136' that may be mechanically coupled to the backplane 180' in any suitable manner, for example, with fasteners or the like. As shown, the actuator 136' may include a solenoid, and may be powered and controlled in any suitable manner and may be electrically coupled to the backplane 180' in any suitable manner, for example, via an electrical connector 135' and wires (not shown). The actuator 136' may include a shot pin 138' that is biased to a normally retracted position, for example by a spring 137' that may be retained between a housing of the actuator 136' and a circlip coupled to a rearward end of the shot pin 138'.

A forward end of the shot pin 138' may be coupled to a lever 145', which may be pivotably coupled to the backplane 180 via a pivot bracket 147'. The bracket 147', in turn, may be coupled directly to the backplane 180 in any suitable manner, for example, by pins 149' extending therethrough as shown in FIG. 3E. As also shown in FIG. 3E, the lever 145' includes a front end 151' having a bayonet with a barb. The barb may be used to engage against an inside surface of the rear cover 107' of the cassette 100. The lever 145' may be pivotably fastened to the pivot bracket 154, for example, with a screw, and includes a rear end 155' coupled to the forward end of the shot pin 138' in any suitable manner. For example, the shot pin 138' may extend through a passage in the rear end 155' and the rear end 155' may be trapped between a push circlip 167' coupled to the shot pin 138' and a pull cap 169' coupled to an end of the shot pin 138' in any suitable manner.

In operation, an attendant may use a touchscreen of the computer 50 to request unlocking of the cassette and, in turn, the computer 50 may send any suitable signal(s) to the actuator 136', for example, via a dedicated output for each cassette via an input/output rack of the apparatus 10. The signal(s) serve to advance the shot pin 138' against the bias force of the retracting spring 137'. Accordingly, the push circlip 167' pushes on the rear end 155' of the lever 145' to pivot the lever 145' so that the front end 151' disengages from a rear inside surface of a rear wall of the rear cover 107'. At this point, the cassette 100' may be pulled away from the backplane 180' wherein the front end 151' passes through an opening in the rear wall of the rear cover 107' and the connectors 140' and 141' disengage. The solenoid signal(s) may cease after a predetermined amount of time, or after the computer senses disengagement of the electrical connectors 140', 141', and then the spring 137' retracts the shot pin 138' to return the lever 145' to a lock-ready position. In this position, when the cassette 100' is advanced toward the backplane 180' to a closed position, a cam surface of the front end 151' contacts the rear cover 107 at the opening thereof such that the front end 151' raises and passes through the opening. As the cassette 100' continues advancing and nears its closed position the connectors 140', 141' fully engage and the barb of the front end 151' drops behind a portion of the rear wall of the rear cover 107' to lock the cassette 100' in place.

At this point, the computer recognizes the cassette using, for example, any suitable plug-and-play utility like USB, or the like. In other words, the connectors 140', 141' may be configured as part of a cassette presence detection device wherein the computer recognizes that the cassette is engaged to the apparatus 10' when the connection between the connectors 140', 141' is made. For example, the computer 50 may periodically poll the memory devices 142 via the connectors 140', 141' and read serial numbers and other data of the memory devices 142.

Figure 3H:
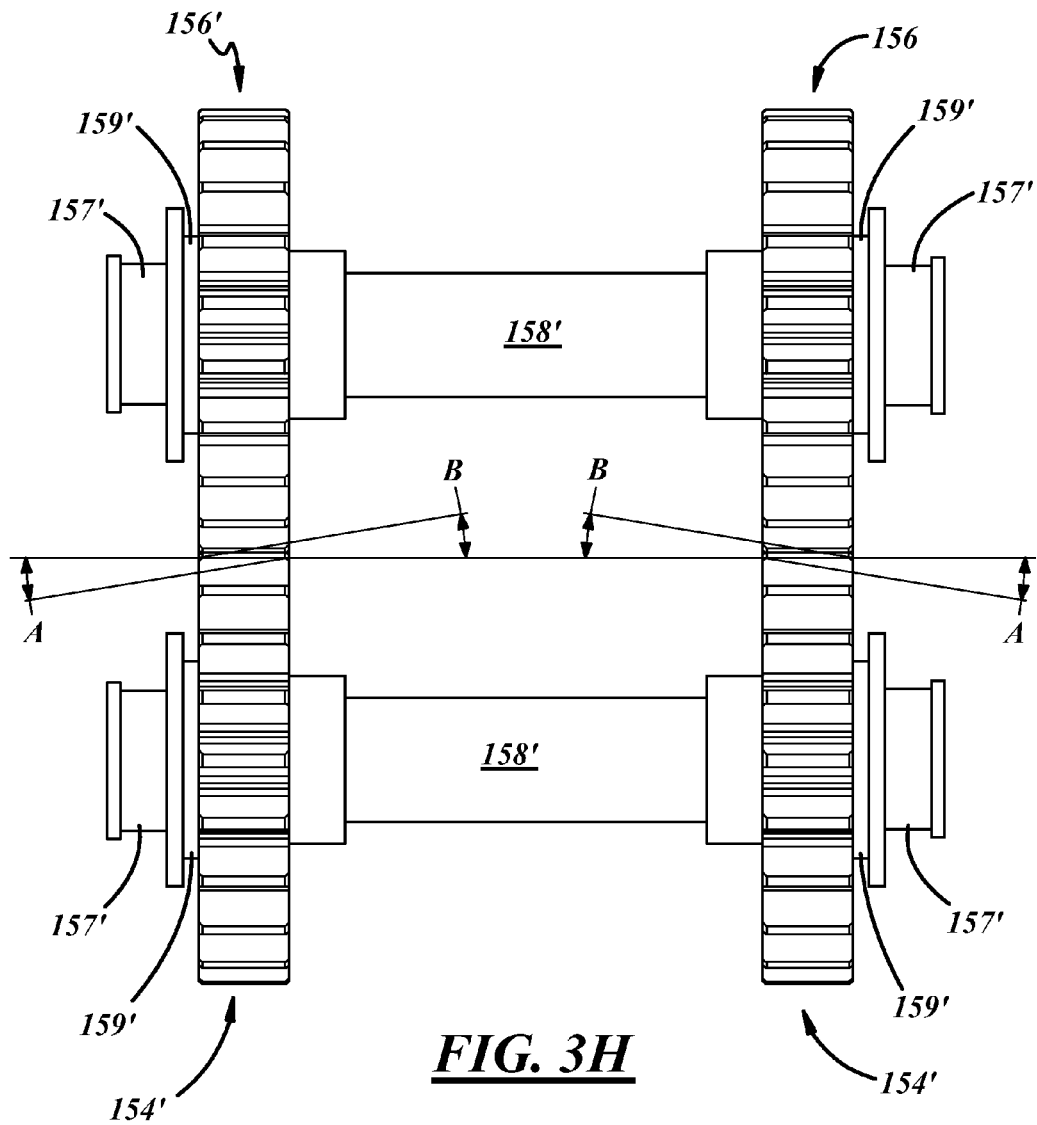
FIG. 3H is a front view of an exemplary embodiment of a portion of an alternative material handling apparatus for the cassettes of FIGS. 2A and/or 3A.

FIG. 3H illustrates a portion of a drivetrain particularly configured to feed media in a straight path through the slot 101' of the cassette 100' (FIG. 3A). The drivetrain includes the drive elements 154' carried on a respective one of the drive axles 158, and driven elements 156' carried on an driven axle and cooperatively engaged with the drive elements 154'. The elements 154' and 156' may be configured to pull the media in opposing directions transverse to the feed direction of the media. This prevents the media from tracking to one side or the other and from binding between inboard sides of the elements 154', 156'.

In one exemplary embodiment, as exaggerated in FIG. 3H, outer surfaces of the drive elements 154' may be tapered at angles A from larger diameters at inboard sides of the elements 154' to smaller diameters at outboard sides of the elements 154'. Conversely, outer surfaces of the driven elements 156' may be tapered at angles B from smaller diameters at inboard sides of the elements 156' to larger diameters at outboard sides of the elements 156'. Accordingly, the elements 154' and 156' are provided with opposing tapers. According to this embodiment, the angles A and B may be of the same magnitude, for example, two to five degrees. In a variation of this embodiment, elements 154' and 156' may be provided with like tapers, wherein the outer surfaces of the driven elements 156' may be tapered from larger diameters at their inboard sides to smaller diameters at their outboard sides. In another embodiment, the outer surfaces of the elements 154', 156' may be generally cylindrical instead of tapered and the gear teeth may be helical, or disposed at an angle. Helix angles of the gear teeth may be the same magnitude between the elements 154' and 156'. In either embodiment, the elements 154', 156' may be composed of any suitable material, for example, NYLON or any other suitable durable plastic.

Figure 3I:
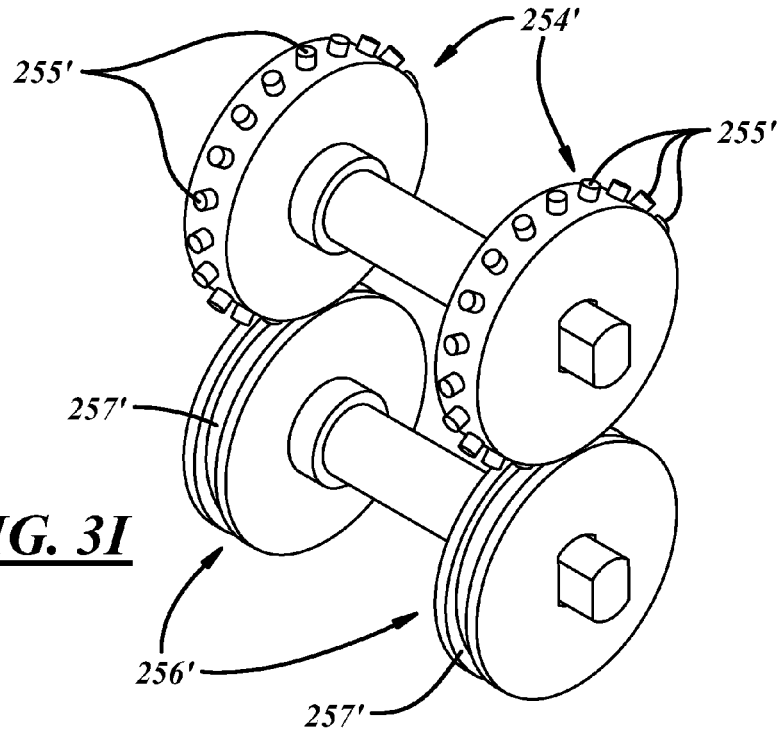
FIG. 3I is a perspective view of an exemplary embodiment of a portion of another alternative material handling apparatus for the cassettes of FIGS. 2A and/or 3A.

In a further exemplary embodiment of a drivetrain, FIG. 3I illustrates drive elements 254' operatively coupled to driven elements 256' for feeding a strip of packaged medication therebetween. The drive elements 254' include a plurality of circumferentially spaced and radially extending pegs 255' and the driven elements 256' include annular grooves 257' to receive the pegs 255' therein as the elements 254' rotate. Accordingly, the elements 254' 256' may constitute a pinwheel type of drivetrain having pinwheel drivetrain elements to feed a strip of packaged medication.

Figure 3K:
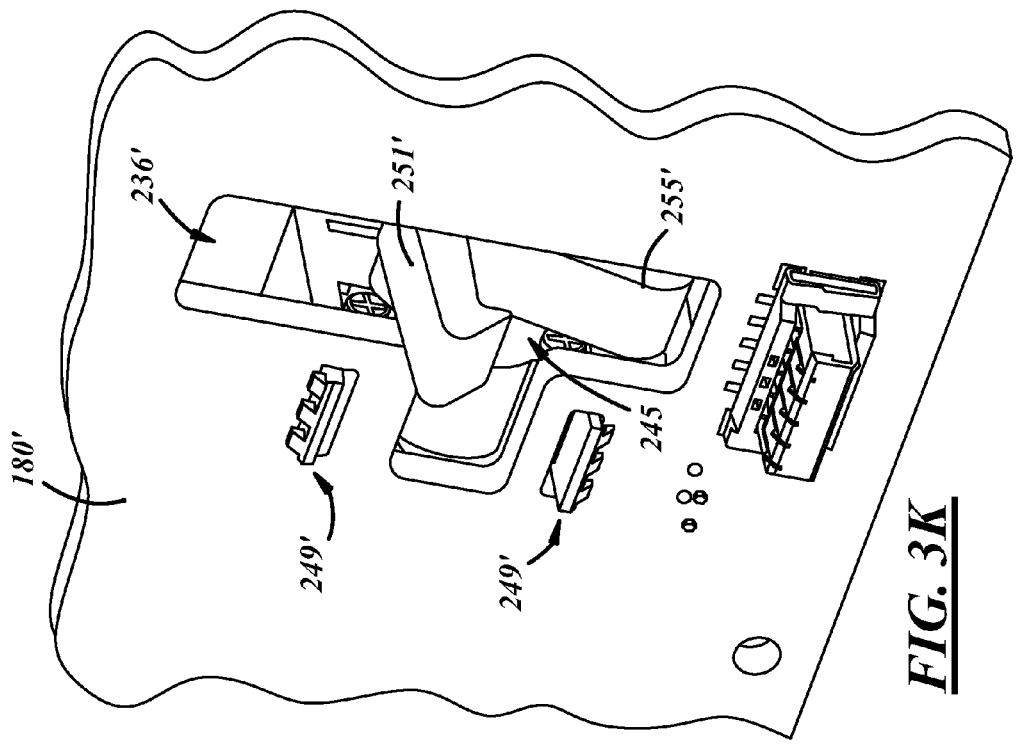
FIG. 3K is a fragmentary perspective front view of the locking apparatus portion of FIG. 3J.
Figure 3J:
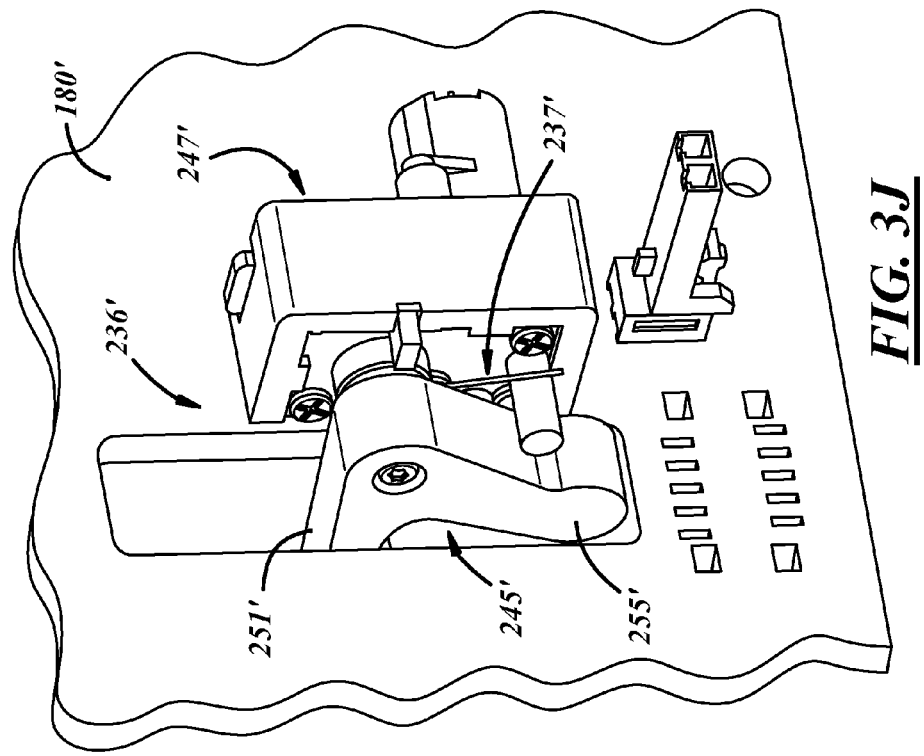
FIG. 3J is a fragmentary perspective rear view of another embodiment of a locking apparatus portion that may be used with the cassette of FIG. 3A.

FIGS. 3J-3K illustrate another exemplary embodiment of a locking apparatus portion that may be used with the cassette 100' of FIG. 3A. This embodiment is similar in many respects to the embodiment of FIGS. 2A-3G and like numerals between the embodiments generally designate like or corresponding elements throughout the several views of the drawing figures. Additionally, the descriptions of the embodiments are incorporated by reference into one another and the common subject matter generally may not be repeated here.

The locking apparatus portion of FIGS. 3J and 3K illustrate an electromechanical actuator 236'. The actuator 236' may include a motor and drivetrain coupled to the motor, wherein the motor may be powered and controlled in any suitable manner and may be electrically coupled to the backplane 180' in any suitable manner. For example, the actuator 236' may include a GM 10 geared pager motor product available from Solarbotics of Calgary, Canada. The actuator 236' may be mechanically coupled to the backplane 180' in any suitable manner, for example, with a bracket 247' having clip portions 249' extending through the backplane 180' as shown in FIG. 3K. An output shaft of the drivetrain may be coupled to a lever 245'. As also shown in FIG. 3K, the lever 245' includes a first leg 251' having a bayonet end with a barb. The lever 245' also includes a second leg 255' that may double as a reaction member and as a cassette ejector.

In operation, when the actuator motor is energized it rotates to cause the drivetrain shaft and, thus, the lever 245' to rotate in a clockwise direction. As the motor, drivetrain shaft, and lever 245' rotate, the first leg 251' of the lever 245' raises and unlocks the corresponding cassette (not shown here), and also causes the second leg 255' of the lever 245' to push the cassette outward for removal.

When the actuator motor is de-energized, a spring 237' biases the lever 245' back into a lowered or locked position wherein the first leg 251' locks the cassette and the second leg 255' rests against a stop pin 269'. Accordingly, when the cassette is reinserted into a corresponding compartment, the lever 245' will raise and snap back against an inside surface of the rear cover of the cassette to lock the cassette to the rest of the apparatus. In one example, the spring 237' may be a torsional spring having one leg, as shown, in contact with the stop pin 269' and another leg (not shown) in contact with the lever 245'. However, any other suitable spring arrangements may be used to bias the lever 245' to a normally locked position.

In general, the components of the apparatuses 10, 10' may be manufactured according to techniques known to those skilled in the art, including molding, machining, stamping, and the like. Also, the apparatuses 10, 10' may be assembled according to known techniques. Likewise, any suitable materials can be used in making the components, such as metals, composites, acetal polymers or other polymeric materials, and the like.

Figure 4B:
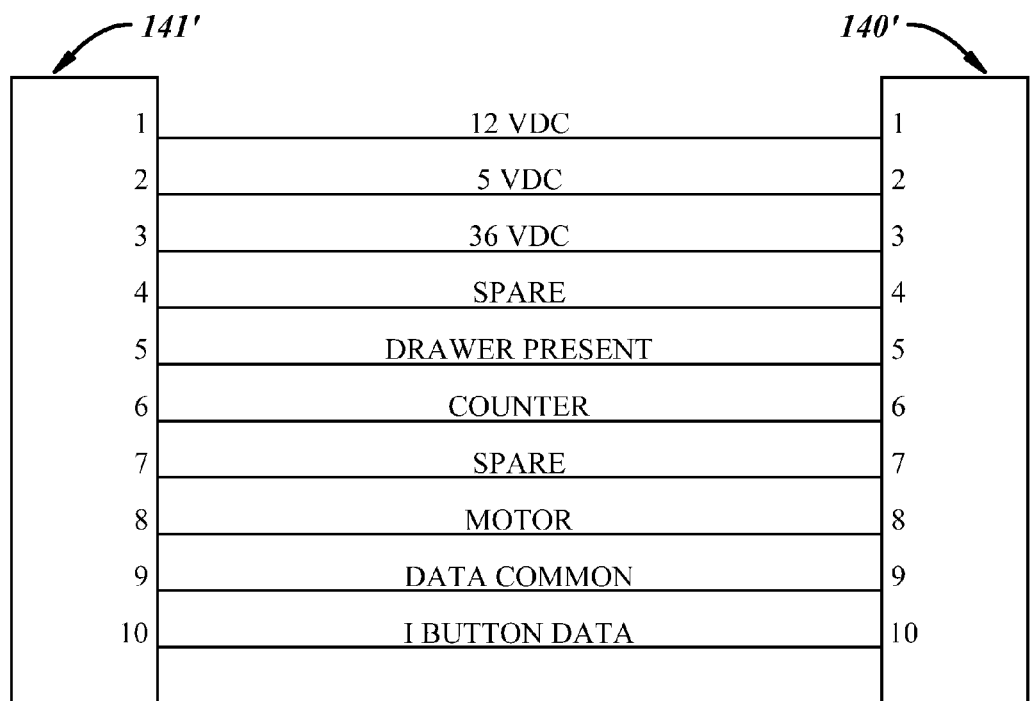
FIG. 4B is a schematic of another embodiment of electrical connections for the computerized medication administering apparatus of FIG. 1 and the cassette of FIGS. 3A-G.
Figure 4A:
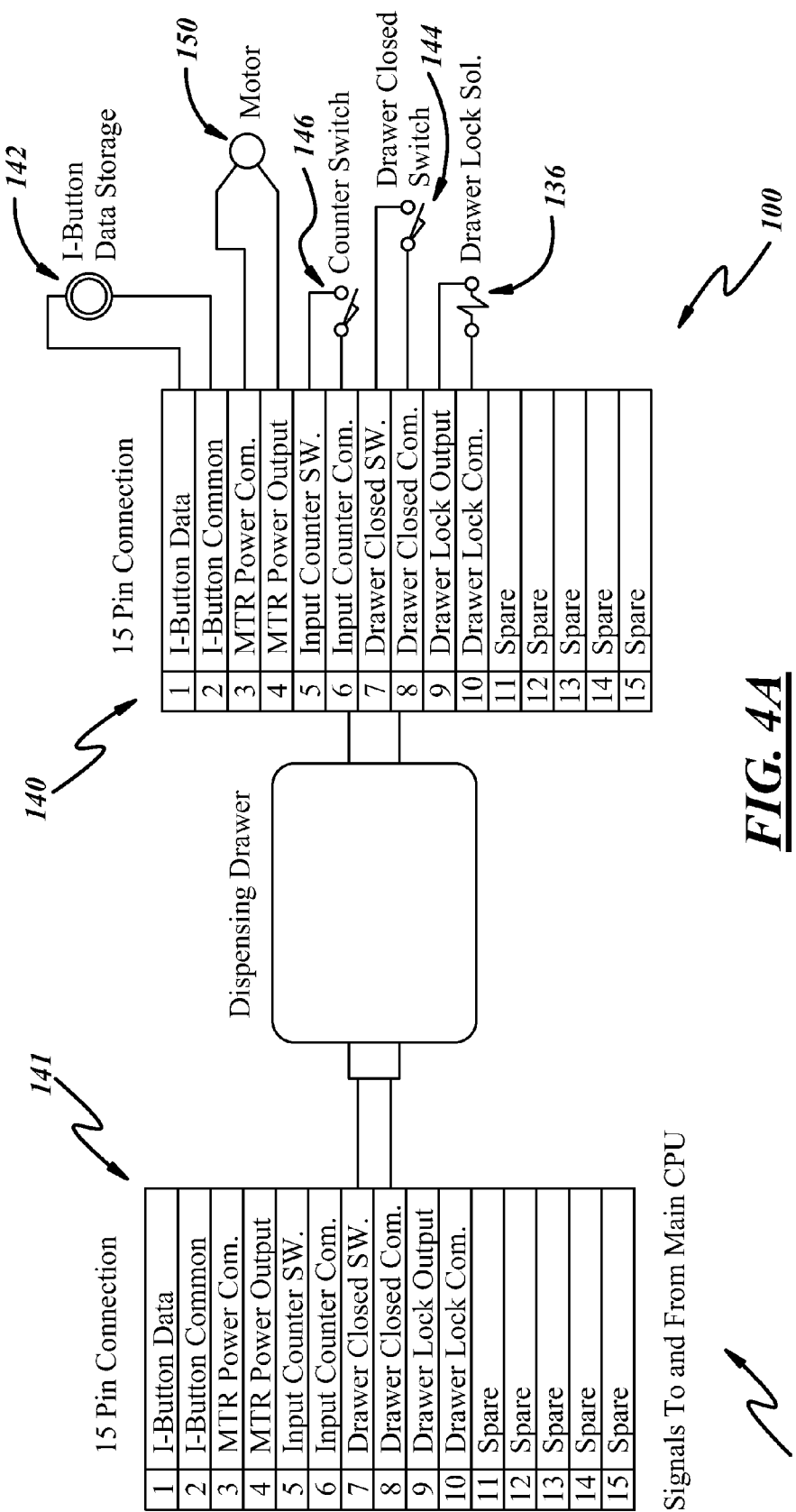
FIG. 4A is a schematic of one embodiment of electrical connections for the computerized medication administering apparatus of FIG. 1 and the cassette of FIGS. 2A-2K.

FIG. 4A illustrates a schematic connector diagram including the connector 140 of the exemplary cassette 100, and the locking actuator 136, the cassette status switch 144, the counter 164, the motor 150, and the memory device 142. Although not shown in FIGS. 2 and/or 3, any suitable power or data wires or the like may be coupled between the aforementioned devices and the connector 140. The connector 140 is adapted to be coupled to the apparatus connector 141 of cart of the apparatus 10. The connectors 140, 141 may be configured as a part of a cassette presence detection device wherein the computer 50 recognizes that the cassette 100 is engaged to the apparatus 10 when the connection between the connectors 140, 141 is made. This may replace or supplement the functionality of the cassette status switch 144.

FIG. 4B illustrates another schematic connector diagram including the connector 140' of the exemplary cassette 100' adapted to be coupled to the apparatus connector 141' of the cart of the apparatus 10. The diagram illustrates example data paths between the connectors 140', 141'.

Referring to FIG. 1, the computer 50 of the apparatus 10 may interact with the touch screen monitor 14, and in some embodiments a conventional mouse or keyboard, input/output cards, and includes a central processing unit and memory. The computer 50 also may include a conventional communications port that permits the computer 50 to be coupled to a conventional modem or other communication device in order to communicate with a pharmacy, physician, and/or doctor's office and to download and/or upload data or information to and/or from the pharmacy, physician, and/or doctor's office. As used herein, the terms data and information are interchangeable.

The administering apparatus 10 may be associated with a pharmacy in any suitable manner. For example, a pharmacy may own or lease the apparatus 10, or may be a service provider to the apparatus 10.

The computer 50 may be communicated in any suitable manner to any device of the cassettes 100, for example, switches, motors, memory devices, etc. The computer 50 may also be constructed and arranged to communicate with a shared computer server or to a web-based application for communicating with a doctor's office, physician, pharmacist, another case facility, nurse's station and the like.

Figure 5:
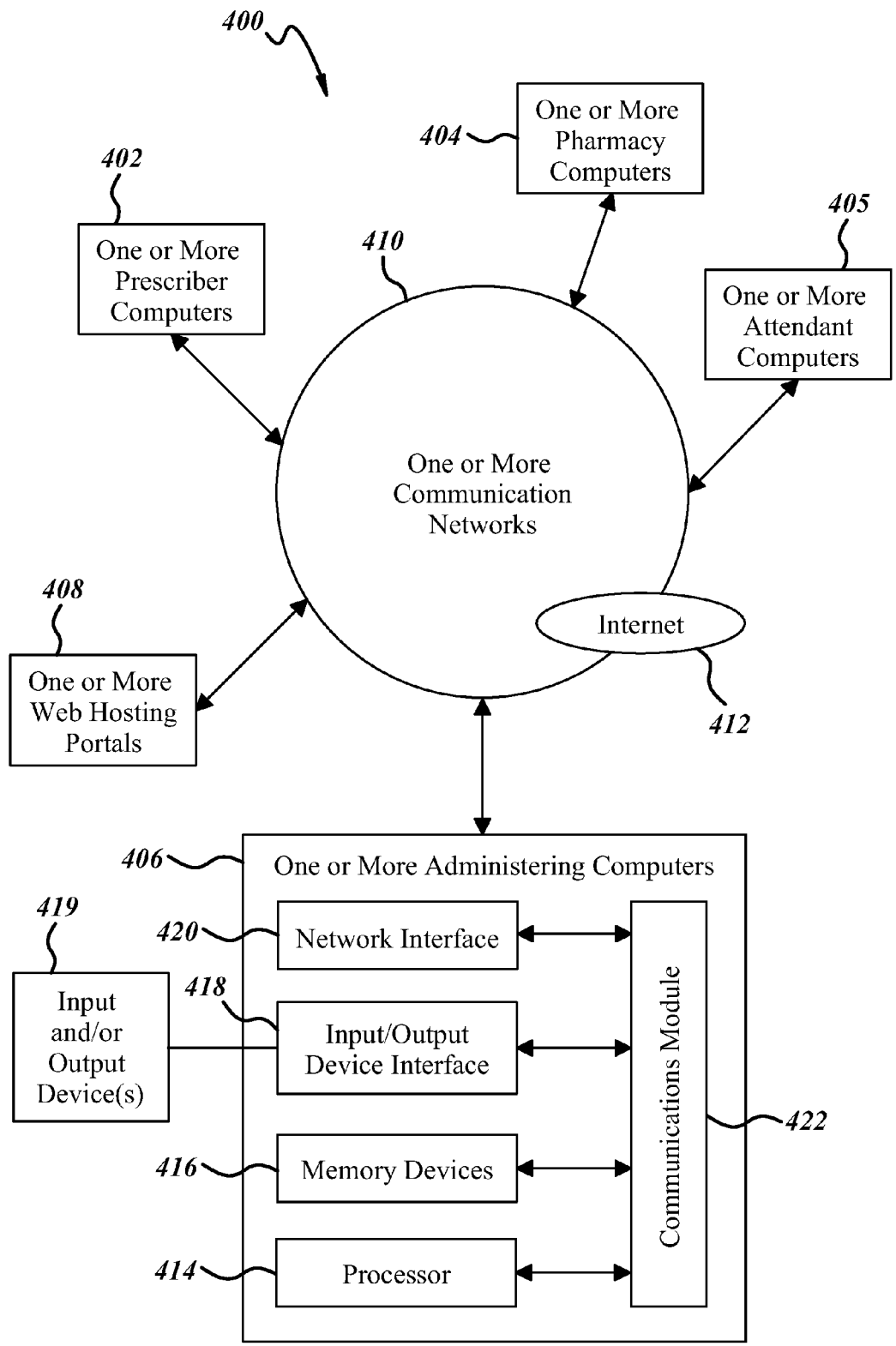
FIG. 5 is a block diagram illustrating a computing system according to one exemplary embodiment.

FIG. 5 shows one example of a system 400 to implement method and/or apparatus aspects of the present disclosure. The system 400 may include one or more of the following subsystems, or system elements or components: one or more physician or prescriber computers 402 for receiving, processing, and transmitting data; one or more pharmacy computers 404 for receiving, processing, and transmitting data; one or more nurse or attendant computers 405 for receiving, processing, and transmitting data; one or more administering computers 406, which may include the aforementioned computer 50, for receiving, processing, and transmitting data; one or more web-hosting servers 408 that may host one or more websites or network portals; and one or more communication networks 410, which may include a wide area network (WAN), for example the Internet 412, for providing communication among the various system elements. Those of ordinary skill in the art will recognize that the various computers 402, 404, 406, 408 may have hardware and software aspects in common, which will not be repeated for each computer description. Accordingly the descriptions of the various computers are mutually incorporated by reference.

Although the system 400 may include computers, for purposes of this disclosure, the system 400 may include any instrumentality or aggregation of instrumentalities operable to compute, classify, detect, display, handle, originate, manipulate, manifest, process, record, reproduce, receive, retrieve, switch, store, or utilize any form of data, information, intelligence for academic, business, production, scientific, or other purposes. Although described in connection with an exemplary computing system environment, the disclosed methods may be operational with numerous other special purpose computing system environments or configurations. The computing system environment is not intended to suggest any limitation as to the scope of use or functionality of the system or method.

Moreover, the computing system environment should not be interpreted as having any dependency or requirement relating to any one component, or combination of components, illustrated in the exemplary operating environment. Examples of well known computing systems, environments, and/or configurations that may be suitable for use include, but are not limited to, personal computers, server computers, hand-held or laptop devices, multiprocessor systems, microprocessor-based systems, set top boxes, programmable consumer electronics, personal digital assistants, mobile telephones, network PCs, minicomputers, mainframe computers, distributed computing environments that include any of the above systems or devices, and/or the like.

In general, the administering computer 406 may receive input from the various devices of the administering apparatus 10 and/or other computers 402, 404, 408, at least partially enable or carry out method steps disclosed herein, and transmit output to the various devices of the administering apparatus 10 and/or the various other computers 402, 404, 408. To facilitate such functionality, the administering computer 406 may have a processor 414, one or more memory devices 416 in communication with the processor 414 such as an internal memory and/or an external memory, an input/output device interface 418, a network interface 420, and a communications module 422.

The communications module 422 may be any type of suitable module including a system bus, which may couple one or more of the various above-described system components or modules. The system bus may provide for data transmission internally between the elements in the computer and externally between the internal elements of the computer 406 and any other elements external of the computer 406.

The processor 414 may be configured to execute instructions or control logic that provides at least some functionality of the disclosed methods. In this respect, the processor 414 may encompass one or more processing units, controllers, microprocessors, micro-controllers, discrete logic circuit(s) having logic gates for implementing logic functions upon data signals, application specific integrated circuits (ASIC) with suitable logic gates, complex programmable logic devices (CPLD), programmable or field-programmable gate arrays (PGA/FPGA), any combinations of the aforementioned, and the like. As used herein, the term processor may also include any ancillary devices such as clocks, power supplies, and the like.

The memory 416 may include computer readable storage or media in the form of removable and/or non-removable, volatile memory and/or non-volatile memory. Exemplary volatile memory may include random access memory (RAM), static RAM (SRAM), dynamic RAM (DRAM), and the like, for running software and data on the processor. Exemplary non-volatile memory may include read only memory (ROM), erasable programmable ROM (EPROM), electrically erasable programmable ROM (EEPROM), dynamic read/write memory like magnetic or optical disks or tapes, and static read/write memory like flash memory, for storing software and data.

The input/output device interface 418 may be used to communicate the administering computer 406 with user selection devices or one or more input peripheral devices 419. Such devices may include a pointing device (e.g., a mouse, trackball, pen, touch pad, touchscreen, or the like), keyboard, modem, internal card reader, and the like, that may be used to enter commands and data into the computer 406. Other input devices (not shown) may include a microphone, joystick, satellite dish, wireless communication device, proximity sensor, scanner, or the like. The input/output interface 418 may connect the above described input devices, and possibly other input devices, to the processor 414 via the system bus 422, but may connect via other interfaces and bus structures, such as a parallel port, Universal Serial Bus (USB), infrared device, or the like.

The input/output device interface 418 may be used to communicate the administering computer 406 with one or more output peripheral devices (not shown). The output peripheral devices may include a printer, a monitor, or other type of display device or other peripheral device such as speakers (not shown), and the like, and also may be connected to the system bus 422 via the input/output interface, which may be any suitable printer, video, etc., type of interface. One example of a combined input/output peripheral device includes the touch screen monitor 14 of the administering apparatus 10.

The network interface 420 may include any suitable communication device such as a wired or wireless telephone device, dial-up modem, cable modem, or the like for communicating the computer 406 with the communications network 410. The network interface 420 may enable transmission and reception of voice, data, fax, and/or like transmissions to and from the network 410.

As used herein, the term interface broadly means any suitable form of electronic device or adapter, or even a software module or adapter, which enables one piece of equipment to communicate with or control another. Any of the interfaces disclosed herein may conform to any suitable protocols such as Ethernet or field buses such as Profibus, Interbus, Devicenet, RS-232, parallel, small computer interface, USB, wireless protocols such as Bluetooth, infrared, and the like, and any other suitable input/output (I/O) protocols.

As shown, the computer 406 may operate in a networked environment, in communication with one or more remote computers, which may include the prescriber and/or pharmacy computers 402, 404. In any case, the remote computers may be personal computers, servers, routers, network PC's, peer devices, other common network nodes, and the like. In a networked environment, software and/or data used by the computer, or portions thereof, may be stored in the remote computer or a remote memory storage device (not shown) associated therewith or connected thereto. By way of example, and not limitation, remote application programs/data may reside in memory of the remote computer(s).

At least some portion of the disclosed methods may be practiced locally or in a distributed computing environment where tasks may be performed by the various computers 402, 404, 406, 408 that are linked through the communications network 410. In a distributed computing environment, programs may be located in both local and remote computer storage media including memory storage devices. It is therefore to be understood that the presently disclosed methods may be at least partially performed by any computing devices suitable for executing one or more of the specified functions, using any media and being located anywhere.

Computer programs or software may include executable instructions for implementing logical functions and can be embodied in any computer-readable medium for use by or in connection with the processor 414, which may retrieve and execute the instructions. The software may include, but is not limited to routines, modules, objects, components, data structures, and the like, for performing particular tasks and/or implementing particular abstract data types. General examples include software programs comprised of instructions in source code, object code, executable code or other formats; firmware programs; or hardware description language (HDL) files; and the like. Specific examples include assembler, C, C++ objects, C# sharp, object oriented programming, Visual Basic, Visual C++, XML, Java, and Microsoft® (MS) Foundation Classes, Microsoft.net, visual-.net, PERL, PHP, SQL, and/or the like.

In general, the communication network 410 may be any suitable local area network, wide area network including the Internet 412, or the like. The communication network 410 may include a wireless system, land network, any combination thereof, or the like, that is adapted to transmit and receive signals to and from one or more of the prescriber computers 402, pharmacy computers 404, administering computers 406, and or web hosting server 408.

In one specific implementation, the communication network 410 may include a wireless carrier system including a wireless communications carrier, a mobile telephone system, satellite broadcast system, or the like, that may incorporate any type of telecommunications in which electromagnetic waves carry signals over part of or an entire communication path. For example, the wireless carrier system may be implemented as a CDMA, GSM, or other cellular communication system, or any other suitable wireless system.

In another specific implementation, the communication network 410 may also or instead include a land network used to connect the computers 402, 404, 406, and web-hosting server 408. As such, the land network may be a public-switched telephone network (PSTN), an Internet protocol (IP) network, wired network, optical network, fiber network, and/or any combination thereof. The land network may be connected to one or more landline telephones, facsimile machines, computers, or the like.

The network 410 may include a local area network (LAN) and/or a wide area network (WAN), but may also include any other suitable networks, connections, and/or protocols. The LAN and/or WAN may be a wired network, a wireless network, a combination thereof, and the like. When used in a local area networking environment, the computer is preferably connected to the LAN through the network adapter or interface 420. When used in a wide area networking environment, the computer preferably includes the modem or any other means for establishing communications over the WAN. The modem, which may be internal or external, is preferably connected to the system bus via the input interface, or other appropriate arrangement. The network connections shown are exemplary and other means of establishing a communications link between the computers 402, 404, 406 may be used.

The web-hosting server 408 may include one or more communication devices for communicating with the communication network 410, and one or more server computers. The web-hosting server 408 may be directly connected by phone lines, cable lines, fiber optic cable, and/or wirelessly to any suitable land network or wireless network, for example, via the communications network 410. The web server computer may be implemented as any suitable hardware and software capable of providing Internet services to receive and transmit data from and to the computers 402, 404, 406. In an exemplary implementation, the web server 408 may include a computer for executing and storing computer applications, data files or records, and/or databases for managing and storing data supplied by the computers 402, 404, 406.

In various embodiments, the system 400 may be equipped to utilize a variety of communication platforms including the Internet Protocol Suite (commonly TCP/IP) which is the set of communications protocols used for the Internet and other similar networks. The Internet Protocol Suite, like many protocol suites, may be viewed as a set of layers. Each layer solves a set of problems involving the transmission of data, and provides a well-defined service to the upper layer protocols based on using services from some lower layers. Upper layers are logically closer to the user and deal with more abstract data, relying on lower layer protocols to translate data into forms that can eventually be physically transmitted.

RS232 is one exemplary protocol that may be utilized which is an asynchronous serial communication method. The word serial means, that data is sent one bit at a time. Asynchronous tells us that the data is not sent in predefined time slots. Data transfer can start at any given time and it is the task of the receiver to detect when a message starts and ends. Asynchronous communication has some advantages and disadvantages which are both discussed in the next paragraph.

Bluetooth may be utilized which is a wireless protocol utilizing short-range communications technology facilitating data transmission over short distances from fixed and/or mobile devices, creating wireless personal area networks (PANs).

Wireless communication such as WCTP may be utilized. WCTP is called a "transfer" protocol in that it is transferring data content between wire line and wireless systems. The manner in which the WCTP-defined operations are transported between a pair of systems is independent of WCTP syntax. Although any number of transport protocols may be used to move WCTP operations between systems, for example HTTPS, secure socket layer (SSL), or the like, the Hypertext Transfer Protocol (HTTP) has been selected as the recommended transport protocol for WCTP. HTTP was selected because it is already in use.

USB communication may be utilized. Universal Serial Bus (USB) is a serial bus standard to interface devices to a host computer. USB was designed to allow many peripherals to be connected using a single standardized interface socket and to improve the plug-and-play capabilities by allowing hot swapping, that is, by allowing devices to be connected and disconnected without rebooting the computer or turning off the device. Other convenient features include providing power to low-consumption devices without the need for an external power supply and allowing many devices to be used without requiring manufacturer specific, individual device drivers to be installed.

RSS may be utilized. RSS is a family of Web feed formats used to publish frequently updated works such as blog entries, news headlines, and podcasts in a standardized format.

Secure File Transfer Protocol may be utilized. The Secure File Transfer Protocol, or SFTP, is a completely distinct file transfer specification developed by the Secure Shell Working Group and SSH Communications Security Corp. Built on the Secure Shell (SSH) Protocol, the purpose of the protocol is to provide the ability to have secure, efficient, file transfer occurring over an SSH encrypted pipe or tunnel. The general idea is to connect to a remote SSH/SFTP server on port 22, perform a secure SSH v2 handshake with the remote server, and then all future communications would take place through the existing encrypted tunnel. No new connections would need to be established, as they are when using FTP. Alternatively, Secure Sockets Layer (SSL) protocol may be used, or any other suitable secure protocol.

Another example protocol that may be used is Web-based Distributed Authoring and Versioning (WebDAV), which is a set of extensions to the Hypertext Transfer Protocol (HTTP) that allows users to edit, publish, and manage files collaboratively on remote World Wide Web servers.

In one embodiment, the administering apparatus 10 may include a biometric security device coupled to the administering computer 406 to verify proper identification of an administering attendant who is to administer medication or a patient who is to receive administered medication. The biometric security device(s) may be represented by one or more of the system input devices (419, FIG. 4) and may be used to identify the administering attendant as he/she approaches the administering apparatus 10 as an initial passive security measure, and to receive access verification from the administering attendant (e.g. a password, or a biometric input) as a secondary active or passive security measure. The biometric security device may operate using physiological and/or behavioral criteria. Examples follow.

In a first example, an algorithm may be provided to analyze the relative position, size, and/or shape of the eyes, nose, cheekbones, and jaw. These features are then used to search for other images with matching features used to identify distinctive features on the surface of a face, such as the contour of the eye sockets, nose, and chin.

In a second example, fingerprint identification security may be provided. The three basic patterns of fingerprint ridges are the arch, loop, and whorl. An arch is a pattern where the ridges enter from one side of the finger, rise in the center forming an arc, and then exit the other side of the finger. The loop is a pattern where the ridges enter from one side of a finger, form a curve, and tend to exit from the same side they enter. In the whorl pattern, ridges form circularly around a central point on the finger.

In a third example, the major Minutia features of fingerprint ridges are: ridge ending, bifurcation, and short ridge (or dot). The ridge ending is the point at which a ridge terminates. Bifurcations are points at which a single ridge splits into two ridges. Short ridges (or dots) are ridges which are significantly shorter than the average ridge length on the fingerprint. Minutiae and patterns are very important in the analysis of fingerprints since no two fingers have been shown to be identical.

In a fourth example, hand geometry readers may be provided and identifies users by the shape of their hands. Hand geometry readers measure a user's hand along many dimensions and compare those measurements to measurements stored in a file.

In a fifth example, keystroke dynamics uses the manner and rhythm in which an individual types characters on a keyboard, touchscreen, keypad, or any other suitable input device. The keystroke rhythms of a user are measured to develop a unique biometric template of the users typing pattern for future authentication. Raw measurements available from most every keyboard can be recorded to determine dwell time (the time a key pressed) and flight time (the time between "key down" and the next "key down" and the time between "key up" and the next "key up"). The recorded keystroke timing data is then processed through a unique neural algorithm, which determines a primary pattern for future comparison.

In a sixth example, hand vein identification may be provided. The dorsal venous network of the hand is a network of veins formed by the dorsal metacarpal veins. It is found on the back of the hand and gives rise to veins such as the cephalic vein and the basilic vein.

In a seventh example, iris recognition means may be provided that uses pattern recognition techniques based on high-resolution images of the irises of an individual's eyes. The only biometric authentication technology designed for use in a one-to many search environment, a key advantage of iris recognition is its stability, or template longevity as, barring trauma, a single enrollment can last a lifetime.

In an eighth example, retinal scan identification may be provided and used to map the unique patterns of a person's retina. The blood vessels within the retina absorb light more readily than the surrounding tissue and are easily identified with appropriate lighting. A retinal scan is performed by casting an undetectable ray of low-energy infrared light into a person's eye as they look through the scanner's eyepiece. This beam of light outlines a circular path on the retina. Because retinal blood vessels are more sensitive to light than the rest of the eye, the amount of reflection fluctuates. The results of the scan are converted to computer code and stored in a database.

In a ninth example, signature identification means may be provided. A signature is a handwritten (and sometimes stylized) depiction of someone's name, nickname or even a simple "X" that a person writes on documents as a proof of identity and intent. The writer of a signature is a signatory. Like a handwritten signature, a signature work describes the work as readily identifying its creator.

In a tenth example, voice identification means may be provided. Speaker recognition (also known as voice recognition) is the computing task of recognizing people (which may involve identifying them and/or authenticating their identity) from their voices. Such systems extract features from speech, model them, and use them to recognize the person from his/her voice.

In an eleventh example, facial thermograph identification means may be provided. Infrared thermography, thermal imaging, or thermal video, is a type of infrared imaging science. Thermographic cameras detect radiation in the infrared range of the electromagnetic spectrum (roughly 900-14, 000 nanometers or 0.9-14 μm) and produce images of that radiation.

In twelfth example, odor identification means may be provided. An odor is a volatilized chemical compound, generally at a very low concentration, which humans and other animals perceive by the sense of olfaction. Odors are also called smells, which can refer to both pleasant and unpleasant odors.

In a thirteenth example, DNA identification may be provided. Deoxyribonucleic acid (DNA) is a nucleic acid that contains the genetic instructions used in the development and functioning of all known living organisms and some viruses. The main role of DNA molecules is the long-term storage of data. DNA is often compared to a set of blueprints or a recipe, since it contains the instructions needed to construct other components of cells, such as proteins and RNA molecules. The DNA segments that carry this genetic information are called genes, but other DNA sequences have structural purposes, or are involved in regulating the use of this genetic information.

In a fourteenth example, gait identification means may be provided. Gait analysis is the study of animal locomotion, including locomotion of humans.

In one embodiment, tamper devices and alarms may be designed into the system to alert personnel that security of the administering apparatus is being compromised. Such peripheral equipment may be represented by one or more of the input devices (419, FIG. 5). The alarm may be set off by one or more of three different alerts: 1) when an attempt is being made to forcibly remove a cassette from the administrating apparatus when the cassette has not been unlocked, wherein the cassette will travel a predetermined distance before a switch is tripped to set off an alarm; 2) when an attempt is being made to forcibly remove medication from the apparatus out of the cassette, wherein output from the medication administering position counter is sensed by the computer 50 when the material handler has not been triggered to move and the output from the counter is used to set off an alarm; or 3) the administering apparatus has been tipped from its normal horizontal position, wherein a level sensor is tripped to set off an alarm. For example, the level sensor may include a merque level sensor that monitors that the cart is level with the horizontal plan of the earth.

In one embodiment, the administering apparatus 10 may include or be coupled to a care proximity sensing device, which may be one of the input devices (419, FIG. 5). Proximity sensing is the ability of the administering apparatus to tell when a person, other than someone who has present authorized access to the apparatus, is near/in front or the administering apparatus. One or more proximity sensors may be placed on the apparatus 10 in any suitable positions to avert sensing of someone who has present authorized access to the apparatus and to actually sense someone other than the presently authorized user and who may be standing behind or to the side of the authorized user in a position to view the touchscreen of the apparatus. This sensing leads to power down of the touchscreen to keep patient information from being read off the touchscreen by people passing by. A photoelectric, electromagnetic, or the like, proximity sensor may be used and may include a light-beam generator, a photo detector, a special amplifier, and a microprocessor. The light beam reflects from an object and is picked up by the photo detector. The light beam is modulated at a specific frequency, and the detector has a frequency-sensitive amplifier that responds only to light modulated at that frequency. This prevents false imaging that might otherwise be caused by lamps or sunlight.

Figure 6:
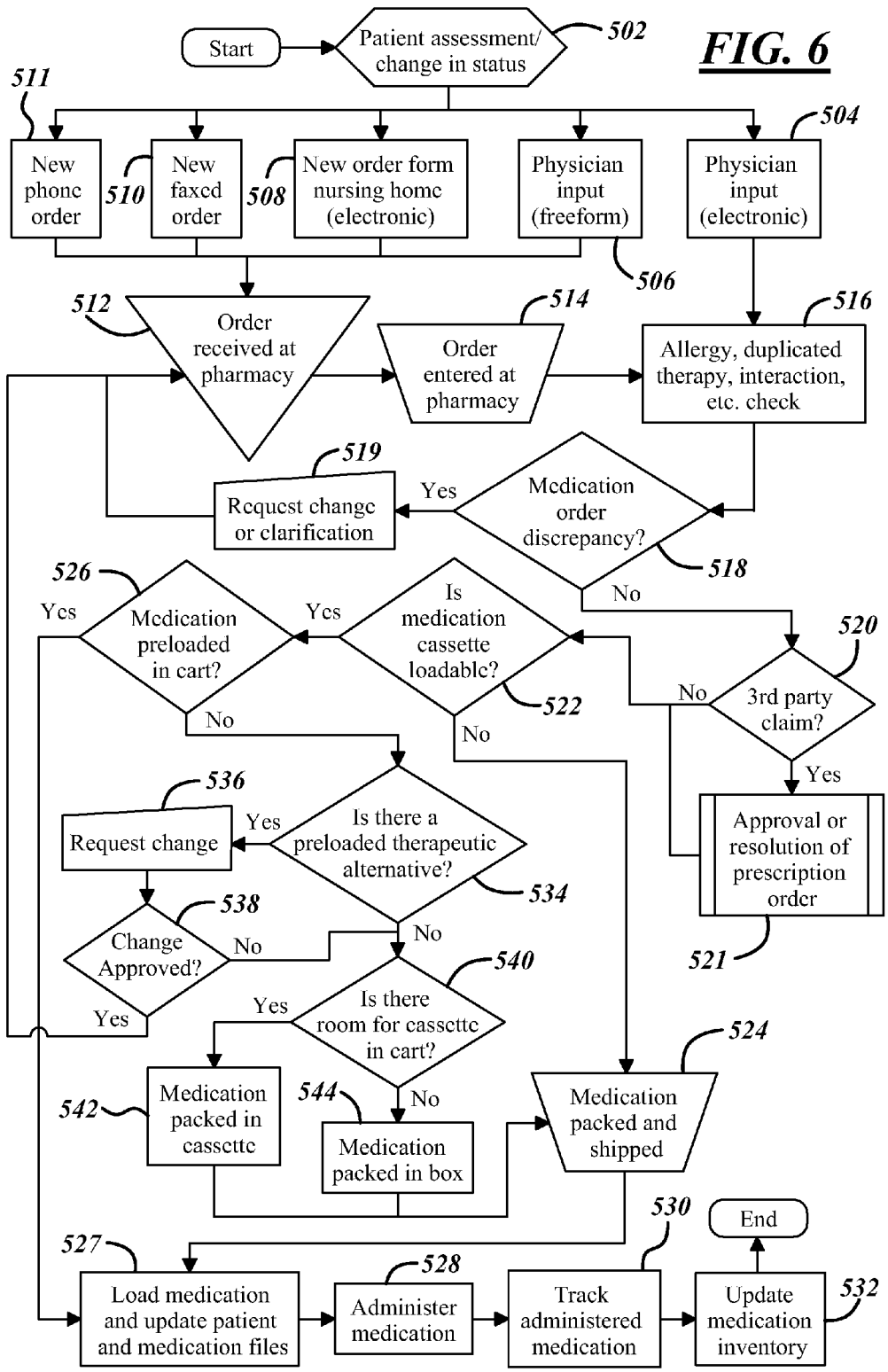
FIG. 6 is a flow chart illustrating a medication management method according to one exemplary embodiment.

Referring now to FIG. 6, one embodiment includes a method of managing medication that may be at least partially enabled or carried out as one or more computer programs within the operating environment of the apparatus 10 and system 400 described above with respect to FIGS. 1-5. Those skilled in the art will also recognize that a method according to any number of embodiments may be carried out using other engine systems within other operating environments. In FIG. 6, an exemplary method 500 is illustrated in flow chart form. As the description of the method 500 progresses, reference may be made to the apparatus 10 and system 400 of FIGS. 1-5.

At step 502, a patient in a medical facility may be medically assessed. The patient may be received as a transfer patient, as a new or intake patient, and with or without complaint of a pre-existing condition. In one example, a medical attendant, for example, a nurse, nursing assistant, physician's assistant, or the like, may initially assess the patient to determine one or more medical conditions of the patient. Also, documentation of a patient assessment may be generated. For example, the medical attendant may generate hardcopy or electronic documentation detailing the one or more medical conditions.

Actual patient data may be stored in computer memory, for example as patient data files or records in the memory 416 of the administering computer 406 or any other suitable computer memory of the system 400. For example, medical data or information of the patient may be stored in Electronic Medical Record (EMR) or electronic Medical Administration Record (eMAR) format. EMR may include demographics, historical medical information, patient allergies, X-rays, physicals results, nursing notes, physician notes, billing, current and historical medications, procedural information about the patient, or any other suitable patient information. Example information may include, but is not limited to, an actual picture of the patient, a complete list of all medications with or without pictures of medications, a complete history of medication and supplements taken, alterations and adjustments, compliance and deliveries and confirmations adherence reporting, current medication orders, and schedule/calendar documentation. Similarly, eMAR data may include specifics as to who administered what medication to whom and when and in what quantity. In particular, such eMAR data may be entered into the administering computer 406, for example, as or after medication is administered to a patient from the administering apparatus 10. In one embodiment, eMAR and/or EMR system integration may be provided, wherein eMAR and/or EMR data including information used by doctors or physicians may be electronically transferred to the patients' data files or records. Typical records may include: initial medication schedules, alterations and adjustments, refills, missed medications, and patient responses to questions, and/or the like.

The eMAR and/or EMR data and corresponding eMAR/EMR software programs may be loaded to any of the system computers and, in any event, may be available to any or all of the system computers via the network connections. For example, an eMAR program and database may be loaded to the administering computer 406 for use by an attendant and may be available to the pharmacy computer 404 for use by a pharmacist.

Further, a prescribing medical professional ("prescriber") may evaluate whether to issue a medication prescription or order to a patient. As used herein, the term prescriber may include a physician, medical doctor, or any agent thereof, for example, a physician's assistant, or any other individual authorized to prescribe medication or the like. For example, a physician or medical doctor may be notified and may review the assessment documentation and may consult with the nurse, caregiver, or patient before prescribing treatment. The terminology medication prescription is typically used in an outpatient setting, whereas medication order is typically used in an inpatient setting. As used herein, the terms may be interchangeable.

At any or all of steps 504 through 510, if a prescriber or prescribing medical professional determines that a patient needs a current medication order or requires an order change, then a medication order may be generated or changed and a corresponding order or change order may be submitted to a pharmacy in any suitable manner. The medication order or change order may include a dosing regimen specific to the patient. An example dosing regimen includes one pill of a given medication, taken thrice daily.

In a first example, in step 504, a prescriber may generate and submit a medication order or change order electronically over a network to a pharmacy in a network online embodiment. In a more specific example, the prescriber may use the computer 402 at the prescriber's location (e.g. office, hospital, nursing home, assisted living center, or clinic) to connect via the network 410, and generate and submit the medication order via the network for review and further action by the pharmacist via the pharmacy computer 404 connected to the network 410.

In this example, the prescriber may have remote access to patient files or records stored in memory 416 of the administering computer 406. Accordingly, the prescriber may access eMAR and/or EMR data, including access to attendant's or nurse's notes about the patient, and to make changes in medication therapy, and the like. More specifically, the prescriber may remotely change medication type, dose, strength, frequency, and the like, and may remotely add or discontinue medication. Accordingly, a prescriber may not only generate a new medication order, but also may change an existing medication order or submit a change order to update the existing medication order.

In a second example, a prescriber may generate a prescription and place a telephone call to the pharmacy to communicate the prescription to the pharmacy as shown in step 506.

In third and fourth examples, a requester (a nurse, administering attendant, or other medical professional, for example) at a medical facility may request a medication refill pursuant to a standing prescriber order. An example would be where a nurse at a nursing home may determine that a patient needs a particular medication reordered. Another example would be where a nurse visiting patients on a room-by-room basis with the exemplary administering apparatus 10 of FIGS. 1-4, finds a particular medication order needs to be refilled and may submit the request from the administering apparatus 10.

In the third example, at step 508, an administering attendant may submit an order via a medication administering apparatus to a pharmacy to administer prescribed medication to a patient according to a dosing regimen of the patient's medication order. For instance, the request may be a network online request over a computer network. More specifically, the requester may use the administering computer 406 at the medical facility to connect to the network 410 to generate and submit the refill order via the network 410 for review and further action by a pharmacist using the pharmacy computer 404 connected to the network 410. In one embodiment, the requester or attendant may use a keyboard and/or a pointing device of the administering computer 406 to submit a new order for eventual authorization by the pharmacy. In another embodiment, the requester or attendant may use any computing device in any suitable manner to connect to the network 410 to submit the new order.

In a fourth example, a requester (e.g. a nurse) at a medical facility may request an existing prescription to be refilled using a fax machine, as shown in step 510. Of course, the nurse may submit the order via telephone as shown in step 511, or by email, verbally, etc, and such a request is considered a network offline request.

At step 512, a medication order may be received at a pharmacy by online network request, by fax, email, or any other suitable manner.

At step 514, a medication order may be entered into a pharmacy computer. For example, a pharmacy technician or pharmacist may enter the data or information from any of steps 506-510 into the pharmacy computer 404 of FIG. 5.

At step 516, a medication order may be checked for interactions with other medications that may be associated with the patient for whom the prescription or order was placed. For example, the pharmacist at the pharmacy may cross-reference all medications being taken by the patient to make sure there are no undesirable or significant drug interactions.

At step 518, a medication order may be verified. For example, the pharmacist at the pharmacy verifies that the order from step 514 was entered correctly. If there is a discrepancy, then the method proceeds to step 519, otherwise to step 520.

At step 519, a change or clarification in an medication order may be requested. For example, a change in the order from step 518 may be requested from and received at the pharmacy at step 512.

At step 520, it may be determined whether or not medication is compensable by a third party. If so, the method proceeds to step 521, otherwise to step 522.

At step 521, payment for a medication order may be approved by or otherwise resolved with a third party, for instance, an insurance company, Medicare, Medicaid, or the like. Any suitable third party payment approval or resolution process may be used. Once approved, or otherwise resolved, then the method proceeds to step 522.

At step 522, it may be determined whether or not the medication for which the requested order was provided is actually loadable to an administering apparatus at a medical facility. For example, some medication may be too bulky or otherwise unloadable to the administering apparatus 10. If not, the method proceeds to step 524, otherwise the method proceeds to step 526.

At step 524, unloadable medication may be packed and shipped to a medical facility for administration in a conventional manner. Thereafter, the method may proceed to step 532, which is described further below.

At step 526, it may be determined whether or not ordered medication is available on or loaded to a medication administering apparatus. For example, a cart database or computer file of the administering computer 406 may be consulted to evaluate the inventory of the medical facility and/or the medication administering apparatus 10, and the location of the medication in the facility and/or on the apparatus 10 may be identified. For example, a pharmacy may poll one or more administering apparatuses at a medical facility. The computers of the polled apparatuses may store data received from and/or associated with the cassettes, or may poll cassette memory to receive such data, which may include medication inventory. The cart database may be updated with data from the cassette memory devices. Accordingly, the pharmacy can determine if medication is available at the medical facility and in what quantity. If it is determined that the medication is not available in a suitable quantity, then the method may proceed to step 552.

At step 527, medication and patient data is updated and/or medication may be loaded to a dispensing apparatus. For example, the pharmacy may use the pharmacy computer 404 to update a patient profile or record and indicate that a patient is to begin or continue receiving ordered medication, wherein the supply of medication on the administering apparatus 10 is to be shared with the patient. The pharmacy may add the ordered medication for the patient to the patient's profile or record, for example, in eMAR software program loaded to the pharmacy computer 404 or to the administering computer 406.

When the patient profile or record is updated, the pharmacy may prospectively charge or bill a predetermined quantity of doses of the ordered medication to the patient or third party, for instance, based on anticipated use over a time period, for example, the following month (i.e. calendar month or next 30 days). For any doses billed before consumption by the patient but not actually consumed by or assigned to the patient, the patient or the third party payer may be retroactively credited for such unused doses. Retroactive crediting may be initiated, for example, upon a change in dosage of medication for a patient, upon patient discharge from the facility, upon discontinuation of medication for the patient, or the like. Such events may be entered manually into the system or may be automatically monitored in any suitable manner.

Also when the patient profile or record is updated, a software program running, for example, on the pharmacy computer 404 or administering computer 406 may include a routine to generate a data file for use by the cart database of the administering computer 406 that may be an SQL database. The data file may include any suitable data, for example, patient name, medication description, GCN code, dosage, and/or the like. For example, an eMAR program may include a routine to generate an XML data file with such data fields. Those of ordinary skill in the art will recognize that such a routine may access such data stored in memory of the pharmacy computer 404 or elsewhere, arrange such data in any suitable format, and save such data as an XML file or the like. The routine may be initiated, for example, whenever the patient profile or record is updated by a sign off or authorization step in an eMAR program. The eMAR program may be PioneerACMS available from New Tech Computers of Shreveport, La., or any other suitable eMAR program. The eMAR program includes its own eMAR database that may be kept separate from the cart database and may also be an SQL database. The eMAR database may include and separately receive facility data, prescriber data, pharmacy data, medication inventory data, patient data, and/or the like.

In another example, the patient profile or record or other patient data may be updated from a location remote from the pharmacy, for example, via a WAN, to allow administration of the medication. For instance, a physician or other suitable professional at a hospital, physician's office, or from a physician's mobile computing device, or the like, may update the patient profile or record to authorize dispensing of the medication to the patient.

In a similar example, a patient's medical record or other patient data may be read or updated from a remote location by a pharmacist, physician, physician's assistant, or the like, for example, via a WAN. In any event, updated patient data may be communicated via the system 400 to the computer 406 of the administering apparatus 10. Also, once the patient data is updated, for example, by the pharmacist and/or physician or other suitable professional, the administering apparatus 10 can provide a notification to an administering attendant that the ordered medication is to be administered to the patient.

In cases where a new cassette has been received from the pharmacy, that cassette may be loaded to the dispensing apparatus 10.

At step 528, an administering attendant (e.g. a nurse) may administer medication to one or more patients at a medical facility using a medication administering apparatus. For example, the attendant may use the touch screen 14 or any other input apparatus to activate the appropriate cassette 100 of the apparatus 10. More specifically, the attendant may log on to the computer 406 in any appropriate manner, for example, using the touch screen 14 to enter username and password or the like. Then, the attendant may use any suitable software (e.g., eMAR software) loaded to the computer 406 to select, look up, or the like a patient from among a plurality of patients at the medical facility. Once the patient is selected, the touch screen 14 may display the medications which are to be administered to the patient at that time. Thereafter, the attendant may select those medications, for example, by tapping on the displayed medications, checking a checkbox with a pointing device, or the like. Once all of the medications are selected, the attendant may instruct the apparatus 10 to convey the selected medications out of their respective cassettes 100, for example, by tapping on an object, soft button, or the like on the touchscreen 14. Software for documenting administration of medication is well known to those of ordinary skill in the art and any suitable such software may be used and/or modified for use. Examples may include such software available from MDI Achieve of St. Louis, Mo., or Artromick International, Inc of Columbus, Ohio.

The administering computer 406 may periodically poll for data files generated by the eMAR program, and may upload or transfer such data files for use with the cart database. For example, the administering computer 406 may run a "FileSystemWatcher" function using a .Net protocol. Once the eMAR file is generated and found, it may be decoded or parsed in any suitable manner for use in scanning the cart database to assess whether or not the authorized medication is available and to determine the location of the medication on the cart.

After receipt of the selections and instructions from the attendant and confirmation of medication on the cart, the computer 406 may send the appropriate signals to the material handlers of the appropriate cassettes 100, for example, via the connectors 140, 141. In general, communication and control between computing devices of medication administering equipment and actuators of such equipment is well known to those of ordinary skill in the art. In response to receiving the signals from the computer 406, the material handlers advance the selected medications out of the slots 101 of the cassettes 100 and, the attendant may then tear or otherwise remove the medication from the cassettes 100. Once the medication has been conveyed out of the cassette 100, the material handler of the cassette 100 inherently locks, for example, by virtue of the worm drive arrangement. The medication M may be provided in strip form with perforations between each unit of medication so that one unit of medication can be removed from the cassette 100 at a time. In the event the perforated strip of medication is insufficient to prevent tampering by itself, the locking material handing apparatus may further prevent someone from pulling additional medication out of the slot 101 of the cassette 100.

A patient in a nursing home or other medical facility may have one or more prescriptions that are dispensed, tracked, and/or serviced in any other way by the pharmacy, and administered by someone at the nursing home. Medication from the pharmacy is stored in and carried by the administering apparatus 10 and is unassigned to any given patient until it is administered. In other words, the administering apparatus 10 stores and administers one or more doses of patient-unassigned medication.

At step 530, administered medication may be tracked. For instance, the dose(s) of medication administered in step 528 may be assigned to the patient to whom it was administered. In one example, the attendant may manually identify and record administered medication in the administering computer 406. In another example, the administering apparatus 10 may automatically verify that a dose of medication was actually administered. For instance, the counter 164 may be coupled to the computer 406, which may increment or decrement a database or computer file to track medication in the cassette from which the medication is administered. In assigning the dose to the patent, a computer file or record associated with the patient and stored in the system 400 may be updated to indicate that medication was actually administered to that patient.

The administered dose(s) may be tracked so that the patient or third party is "net" billed only for actually administered doses. In some situations, the patient may have changes in billing status throughout the month, wherein the third party payer for the patient could be Medicare for a couple of days, then revert to Medicaid or some other payer. Accordingly, by tracking actually administered medication on a dose by dose basis, this system 400 may enable separate and distinct billing of different third party payers on a dose by dose basis. Although, the protocol and procedure for billing third party payers for dispensed medication is generally known, the ability to bill third party payers for only those doses actually taken is not believed to be known. Those of ordinary skill in the art will now recognize that net billing of third party payers for only those doses actually taken may be accomplished by modifications to existing billing systems and software and the like in accordance with the present teachings.

The administration of the dose(s) may also be communicated from the computer 406 of the apparatus 10 to the eMAR database of the pharmacy computer 404 or administering computer 406 in any suitable manner. For example, the communication may include setting a bit of file data associated with the eMAR database, or may simply be availability to the pharmacy computer 404 of the updated patient computer file via the network 410. In another example, the apparatus computer 406 may send a notification, for example, an email or network message to the pharmacy computer 404 in any suitable manner in response to the updating of the patient computer file. In any event, an administration event file (e.g. in XML format) may be generated from the cart database and archived to memory of the computer 406 to include, for example, patient name, room number or other facility location data, drug identification, dosage, quantity, GCN number, NDC number, lot number, date and time of administration, cart identification, cassette identification, and/or the like. The event file may be transmitted from the computer 406 to the pharmacy computer 404 or may be made available to the pharmacy computer 404 via the system 400 in any suitable manner.

The doses also or instead may be tracked to compare a cumulative quantity of administered doses to an authorized quantity of doses under the patient's prescription. For example, variables in a patient's computer file may include the authorized quantity of doses, and the cumulative quantity of administered doses which may be updated in any suitable manner and then compared to the authorized quantity each time the patient is administered a dose. When the cumulative quantity of administered doses equals or exceeds the authorized quantity, then the computer 406 can prevent further administration of that medication to the patient. For example, a flag can be set to prevent operation of the administering cassette that carries the particular medication when administering to the particular patient.

An attendant or other suitable personnel at the medical facility may generate a request for a refill under the particular patient's prescription or order with the pharmacy using the apparatus computer 406, which then may be used to transmit the request over the network 410 where it is received at the pharmacy on the pharmacy computer 404. For example, the transmitting and receiving of the prescription refill request may be facilitated by an Internet website served on the portal 408.

At step 532, inventory of a medication administering apparatus may be updated. For example, a database or computer file may be decremented in any suitable manner to record the administering of medication from step 528. More particularly, one or more medication inventory computer files may be stored on the dispensing apparatus computer 406 or any other system computer and the file(s) may be updated whenever medication is administered.

At step 534, it may be determined whether an alternative or substitute medication is available on an administering apparatus. For example, it may be determined whether other medication that is similar or better than ordered medication may already be loaded to the administering apparatus 10.

If so, at step 536, a medication change request may be submitted to a prescriber. For example, an administering attendant may submit the request using the system 400 via the administering computer 406, and a prescriber may approve the request using the system 400 via the prescriber computer 402.

At step 538, it may be determined whether the change request from step 536 is approved. For example, the administering attendant may receive approval via the computer 406 of the administering apparatus 10 over the network 410. If so, then the method loops back to step 512. If not, for example, because the alternative is preapproved, and/or the patient pays cash, has an account with the pharmacy, and/or otherwise does not require third party approval and/or payment, then the method proceeds to step 540.

At step 540, it is determined whether or not there is availability on an administering apparatus to accept a new or replacement cassette. If so, then the method proceeds to step 542 wherein the pharmacy packs medication into a cassette, and then on to step 524 wherein the medication is prepared for shipment and shipped. But if not, then the method proceeds to step 544 wherein the pharmacy packs medication into a box and, thereafter, to step 524 and on to step 527.

At step 542, patient-unassigned medication is packed at a pharmacy into a cassette to be used in a administering apparatus located at a medical facility. Information about the packed medication and the cassette in which the medication is packed is entered into the pharmacy computer 404. Step 542 may correspond to or include steps 602-608 described below.

At step 544, medication may or may not be assigned to a patient and is packed into a box instead of a cassette. The boxed medication may be loaded to a conventional drawer in the administering apparatus 10 or may be loaded to a cassette on site at the medical facility.

Figure 7:
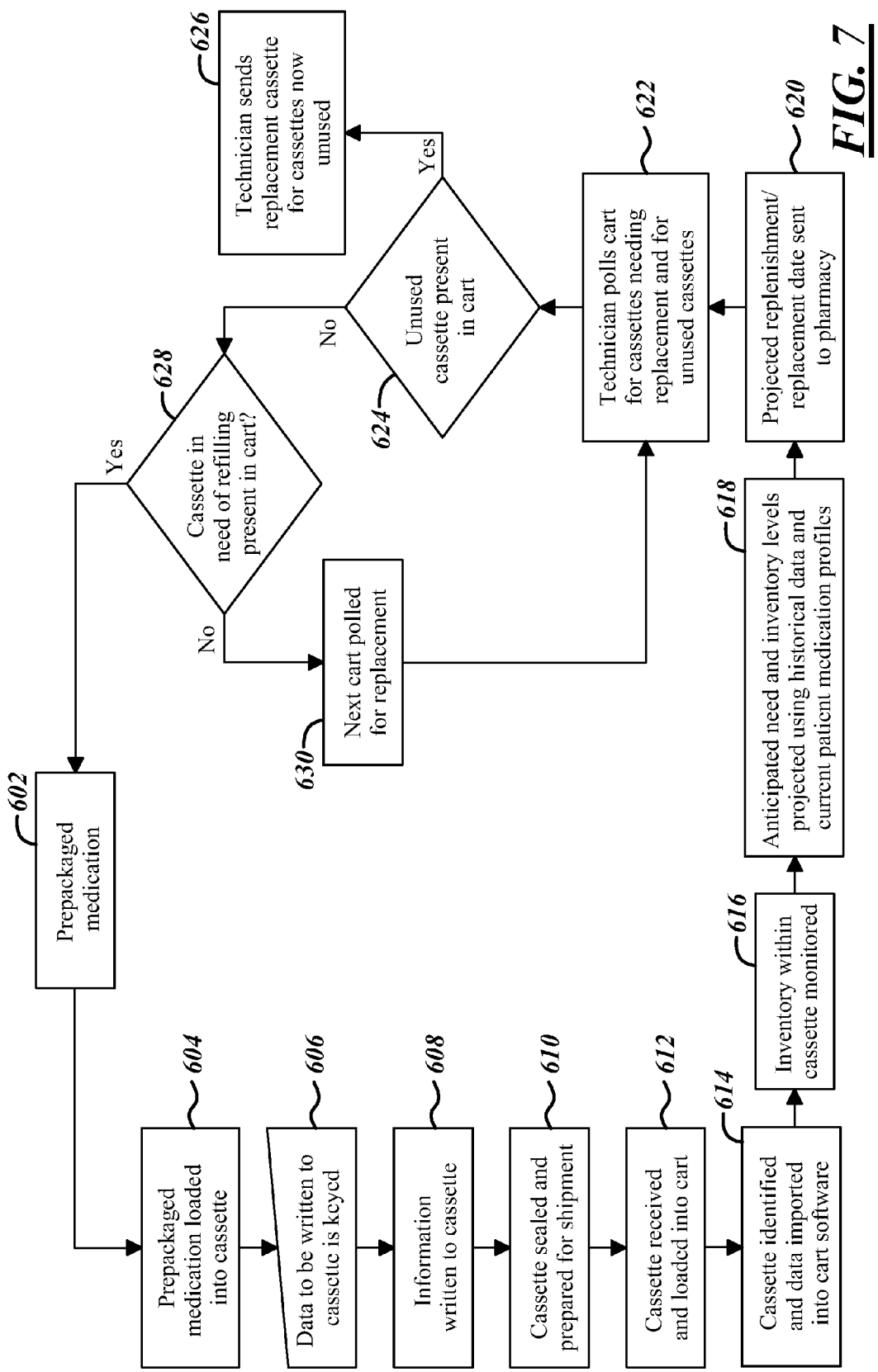
FIG. 7 is a flow chart illustrating a medication management method according to another exemplary embodiment.

Referring now to FIG. 7, a method 600 of managing medication may be provided.

At step 602, medication may be prepackaged. For example, individual pills may be individually packaged in individual compartments of a continuous packaging strip having perforations between the compartments to permit unit by unit administering of medication through the slits 101 of the apparatus 10. The medication may be packaged using any suitable materials and equipment. For example, the medication may be packaged using a paper strip backing thermoformed to a cellophane strip cover using any suitable machinery. The machinery may include a model RX30 produced by G. S. Anderson Manufacturing Co., Inc. of Millbrook, N.Y. and serviced by Norton and Associates of Roswell, Ga., or an AUTO-PRINT brand unit dose packaging system available from Medical Packaging Inc. (MPI) of Ringoes, N.J.

At step 604, medication may be loaded into a medication cassette. For example, the prepackaged medication from step 602 may be packed into one of the cassettes 100 of the administering apparatus 10. However, the medication need not be prepackaged and loose or unpackaged medication may be packed into a cassette.

At step 606, data associated with medication loaded to a cassette may be associated with the cassette. For example, a pharmacist at the pharmacy may enter the data into the pharmacy computer 404. The data may include generic and/or brand name(s) of the medication, manufacturer, lot number, medication description, lot identification, strength of the medication, expiration date, National Drug Code (NDC), a Generic Code Number (GCN), an identifier of a cassette in which the medication will be loaded, the quantity of medication to be initially loaded to the cassette 100, the quantity trip point, and/or the like.

At step 608, data may be associated with a loaded cassette. For example, the data from step 606 may be transmitted to and received by the memory device 142 of the cassette 100 in any suitable manner. For example, the pharmacy computer 404 may be coupled to the connector 140 of the cassette 100 via any suitable cable and connector and data may be downloaded from the computer 404 to the memory device 142 in any suitable manner. In one embodiment, the cassette 100 may be docked in a docking station that mimics a corresponding compartment of the dispensing apparatus 10 and that has a connector corresponding to the cassette connector and coupled to the pharmacy computer 404 in any suitable manner. In a further example, where the device 142 is a device that communicates wirelessly, the computer 404 may download data to the device 142 wirelessly via any suitable wireless communication device(s). In another example, an identification of the cassette 100 may be recorded and associated with the data entered in step 606. For instance, the cassette identification may be recorded manually by the pharmacist viewing an identifier like a serial number or the like on the cassette 100 and entering the identifier into the pharmacy computer 404. Or the identification may be recorded automatically by the pharmacist scanning a barcode, or electronic reader, or the like of the cassette 100 into the computer 404. Such peripheral equipment may be represented by one or more of the input devices (419, FIG. 5). In one embodiment, each cassette 100 in the administering apparatus 10 may have the memory device 142 loaded with a serial number making each cassette 100 unique through the entire supply chain. The pharmacy computer 404 may include all pertinent information regarding the medication for administering in the memory device 142 of the cassette 100.

At step 610, a cassette loaded with medication may be sealed and/or otherwise prepared for shipment or transfer to a medical facility. This step may be the same or similar to step 524 discussed above. The loaded and prepared cassette then may be transferred in any suitable manner to the medical facility including, for example, courier, mail, or the like.

At step 612, a cassette loaded with medication may be received at a medical facility and loaded to an administering apparatus.

At step 614, a received and loaded cassette may be identified and associated with an administering apparatus to which the cassette is loaded. For example, the administering attendant (e.g. nurse) may manually record and enter the identification of the cassette 100 and the location of cassette 100 in the administering apparatus 10 (e.g. A1 or N14). In another example, a barcode, RFID, read/write, EPROM or EEPROM device, or the like of the cassette 100 may be scanned and entered into the computer 406. In another example, the cassette 100 may be coupled to the administering apparatus 10 so that the memory device 142 may be accessed and cassette data may be uploaded automatically into the administering computer 406 upon full insertion of the cassette 100 into its corresponding compartment of the apparatus 10. All records of the cassette 100 and the medication therein may be stored in the administering computer 406 and/or pharmacy computer 404. Such exemplary peripheral equipment enabling this step may be represented by one or more of the input devices (419, FIG. 5).

At step 616, inventory of medication in a cassette may be monitored. An original count of medication loaded to the cassette 100 may be entered into the pharmacy computer 404 separately or as associated with the identification of the cassette 100. Also, medication administered from the cassette 100 may be tracked at the administering apparatus 10. For instance, an automatic counting mechanism, for example, a mechanical, electrical, optical, or magnetic switch, may count each pill or packaged pill administered from the cassette. More specifically, the counter 164 may be coupled to the computer 406, which may increment or decrement a database or computer file to track medication in the cassette 100 from which the medication is administered. Or, an administering attendant may manually record each such administered unit into the administering computer 406.

Also, before an attendant conducts a medication pass ("med-pass"), the attendant may request the dispensing apparatus 10 to compare quantities of medications to be dispensed during the med-pass to actual quantities of those medications actually present on the apparatus 10. In this way, the attendant may ensure that the entire med-pass can be carried out without a need to refill the apparatus before the med-pass is completed. Those of ordinary skill in the art will recognize that the term med-pass means, for example, a discrete round of dispensing medication to one or more recipients. For instance, a med-pass may be a lunchtime med-pass wherein an attendant makes a round through a unit of a facility to dispense medications to various patients in the facility.

At step 618, an anticipated date of depletion of inventory of one or more medications carried on an administering apparatus may be estimated. Accordingly, replacement of one or more cassettes in the administering apparatus may be estimated. For instance, the anticipated depletion and/or replacement date may be estimated based on a patient's historical medication usage, historical usage of medication in the medical facility, anticipated medication usage of patients currently in the medical facility, or projected anticipated use based on patients' current medication orders, or any other suitable criteria, or some combination of the above.

In a first example, a predetermined low level, par value, or trip point may be used to trigger replacement. More specifically, when a count of medication in a cassette falls below the predetermined low level, a replacement estimate notification may be initiated. The medication count may be tracked by any suitable hardware and/or software counting device(s). For example, the counter 164 may be used to decrement a software counter for each cassette each time a unit of medication is administered.

In a second example, a variable low level or trip point may be varied in response to a multiple day or multiple dose rolling average corresponding to usage of a particular medication to estimate when the administering apparatus 10 is expected to be depleted of that medication. More specifically, the low level may be increased as the rolling average increases, and may be decreased as the rolling average decreases. For instance, if a three day rolling average increases to an example 20 pills per day from an example 10 pills per day, then the low level may be increased to an example 60 pills from an example 30 pills. This may facilitate maintaining a desired quantity of days supply (e.g. three days) on the administering apparatus 10 at any give time, regardless of increasing or decreasing demand.

According to the first two examples, the estimate may be communicated online over the network 410 using the system 400. But in a third example, an administering attendant may manually estimate replacement by using professional judgment and by calling, emailing, or faxing the pharmacy with the replacement information. In a fourth example, the estimate may be communicated automatically offline by email, for example. In this example, each time a drug is dispensed, an SQL database in the administering computer 406, for example, may be scanned for the medication dispensed. If that medication is below a predetermined reorder trip point, then an email message may be sent back to the pharmacy via network 410 or Internet 412, for instance, via a wireless communications card of the administering computer 406. For instance, the cart database may be monitored by any suitable routine that checks for cassette's whose medication quantity has fallen below the trip point and communicates a file for use by the eMAR software, which then may automatically generate and transmit an email message to the pharmacy indicating that the cassette is low on medication. Also, the information sent in the email may include facility identification, facility wing, unit, or floor identification, medication identification, GCN code, NDC number fill requirement, and cassette serial number.

At step 620, the replacement estimate may be communicated to a pharmacy, for instance, to facilitate reordering or the like. For example, where the estimate is carried out at the medical facility, the estimate may be communicated from the administering computer 406 to the pharmacy computer 404 via the network 410. However, it is also contemplated that the estimate may be carried out at the pharmacy computer or any other suitable location and need not take place on the administering computer 406. In any case, the estimate may include identifiers for the administering apparatus 10 and the cassette 100, for example, serial numbers. The estimate may also include a replacement quantity, and one or more identifiers for the medication needing replacement.

At step 622, an administering apparatus in a medical facility may be polled for cassettes that may need replacing and/or for unused cassettes. For example, an administering attendant may poll the apparatus 10 at the medical facility, or an individual at some remote location, for instance, a pharmacist at a pharmacy, may poll the cassette 100 via the system 400, or the like. As used herein, the terminology medical facility includes hospital, nursing home, assisted living center, or clinic, or the like. For example, the attendant may manually take inventory of the administering apparatus 10 or may run a routine using the computer 406 to check current inventory levels stored in memory.

At step 624, it may be determined whether or not an unused cassette is present on any administering apparatus in a medical facility. For example, a pharmacy may make the determination via the system 400. If so, then at step 626, the pharmacy may send a replacement cassette for the currently unused cassette.

At step 628, it may be determined whether or not a cassette in need of refilling is present on an administering apparatus. For instance, the pharmacy may make the determination via the system 400. For example, if the quantity of the medication in a given cassette falls below a low limit (par) value, then the method loops back to step 602. Otherwise, a subsequent administering apparatus may be polled for potential replacement of cassette as indicated at step 630.

The methods 500, 600, or any portion thereof, may be performed at least in part as one or more computer programs and the various method steps or instructions may be stored in memory as a look-up table or the like. The computer program(s) may exist in a variety of forms both active and inactive. For example, the computer program(s) can exist as software program(s) comprised of program instructions in source code, object code, executable code or other formats; firmware program(s); or hardware description language (HDL) files. Any of the above can be embodied on a computer usable medium.

One or more of the embodiments above may provide one or more of the features to one degree or another. May provide a unique medication distribution system integrated with a pharmacy, a medical facility (e.g. hospital or nursing home), physician's office, and medication administering apparatus. May enable pharmacists to dispense prescriptions onsite at a medical facility from an offsite pharmacy, pursuant to a physician's medication order. Medication dispensing and packaging may be automated based on each patient's current medication profile, and/or collective medication needs of a group of patients. May allow for actual use packaging, thereby saving labor costs on packaging medication that may never get used. Medications may be made immediately available to a nurse for administration. Medications may be administered as based upon actual need with little or no waste. May enable automatic online documentation of medication administration, antipsychotic behaviors, side effects, etc., by onsite nurse, that may be accessible online by nursing staff, remote pharmacy, and physician's office. May enable online entry and sharing of trending of antipsychotic behaviors and side effects. May enable automated documentation of PRN (as needed) medications as well as required results of administration. May enable recording and tracking of dates and times of administration of medications. May enable electronic billing with ability to net bill a payor for only those doses actually administered. May enable charges for actual doses given to be submitted to proper payor based on coverage at time of administration. May decrease nursing time during the medication pass/administration. May decrease pharmacist time in entering and verifying prescriptions. May decrease pharmacist time in checking prescriptions to be dispensed. May provide automatic documentation of missed doses. May enable medications to be labeled individually at the pharmacy with expiration date and lot number. May eliminate the need for returned medication and associated labor (in those states where mandated or allowed). May eliminate need to transfer orders from the Physician's Orders to the MAR at a nursing home. May automate required medication formulary changes at the point of prescribing. May incorporate direct order entry in the physician's office. Use of common database may eliminate transcription errors. May allow nurse to reorder non-unit dose medications during the pass as needed. May allow nurse to immediately update and transmit to pharmacy changes in patients' Level of Care.

What is claimed is:

1. A method of managing medication using an administering apparatus associated with a pharmacy, comprising:
    storing patient-unassigned medication from the pharmacy in the administering apparatus, wherein the stored medication is not assigned to any patient until the medication is actually administered;
    receiving a medication order at the pharmacy for a patient wherein the medication order includes a dosing regimen specific to a patient; and thereafter
    checking the medication order for interactions with other medications; and thereafter
    updating a patient record to indicate that the patient is to receive the ordered medication from a shared supply of the medication on the administering apparatus; and thereafter
    administering from the administering apparatus a dose of the patient-unassigned medication to the patient having the order with the pharmacy according to the patient's dosing regimen; and then
    assigning the dose of the medication to the patient, including updating the patient record to indicate that the dose of the medication was actually administered to the patient,
    net billing for only doses of medication that are actually administered, wherein a patient or third party is prospectively billed for a predetermined quantity of doses of the medication, and the patient or third party is retroactively credited for any unused doses of the predetermined quantity of doses of medication, wherein the unused doses are not withdrawn from the administering apparatus, and the unused doses are not returned to inventory or discarded.

2. A method as set forth in claim 1 further comprising:
    providing a network including a computer of the pharmacy coupled to a computer of the administering apparatus;
    communicating the administering of the dose from the administering apparatus computer to the pharmacy computer; and
    carrying out the assignment using at least one of the pharmacy computer or the administering apparatus computer.

3. A method as set forth in claim 2 wherein the network further includes a computer of a prescriber and the method further comprises:
    transmitting a prescription from the prescriber over the network; and
    receiving the prescription over the network at the pharmacy.

4. A method as set forth in claim 3 wherein the transmitting and receiving of the prescription is facilitated by a secure Internet website.

5. A method as set forth in claim 2 further comprising:
    transmitting a request for a prescription refill from the administering apparatus to the network; and
    receiving the prescription refill request over the network at the pharmacy.

6. A method as set forth in claim 5 wherein the transmitting and receiving of the prescription refill request is facilitated by an Internet website.

7. A method as set forth in claim 1, further comprising providing a network including a computer of the pharmacy coupled to a computer of the administering apparatus and a computer of a prescriber coupled to at least one of the pharmacy computer or the administering apparatus computer, and the method further comprises allowing the prescriber to access patient records stored in memory of the administering apparatus computer.

8. A method as set forth in claim 7, further comprising allowing the prescriber to make medication changes.

9. A method as set forth in claim 1 further comprising:
    updating an inventory of medication contained in the administering apparatus.

10. The method as set forth in claim 9 wherein quantities of medications to be dispensed during a med-pass may be compared to actual quantities of those medications actually present on the apparatus before the med-pass is conducted.

11. A method of managing medication as set forth in claim 1, and further comprising:
    approving administering of medication to a patient in a medical facility from a administering apparatus;
    determining whether or not the medication is loaded to the administering apparatus;
    if medication is not loaded to the administering apparatus, then determining whether an alternative medication is loaded to the administering apparatus;
    if the alternative medication is loaded to the administering apparatus, then submitting a prescription change request to a prescriber; and
    administering the alternative medication to the patient if the prescriber approves the change request.

12. The method of claim 1 wherein the net billing is carried out on a dose by dose basis to enable separate and distinct billing of different third party payers on the dose by dose basis for only those doses actually administered.

13. A method of managing medication using an administering apparatus associated with a pharmacy, comprising:
    storing medication from the pharmacy in the administering apparatus;
    administering from the administering apparatus a dose of the medication to a patient having a prescription with the pharmacy;
    updating an inventory of the medication in the administering apparatus responsive to the administration of the dose of the medication;
    estimating a date of depletion of the inventory of the medication; and
    stocking the administering apparatus based on the estimated date of depletion.

14. A method as set forth in claim 13 wherein the estimating is carried out based on at least one of historical medication usage in a medical facility in which the administering apparatus is used, current usage of patients who receive medication from the administering apparatus in the medical facility, or projected anticipated use based on patients' current medication orders.

15. A method as set forth in claim 14 wherein the historical medication usage includes a rolling average.

16. The method of claim 15 wherein the rolling average includes a multiple day or multiple dose rolling average corresponding to usage of the medication to estimate when the administering apparatus is expected to be depleted of that medication.

17. The method of claim 16 wherein a medication replacement low level is variable, and responsive to the rolling average wherein the low level increases as the rolling average increases, and decreases as the rolling average decreases.

18. The method of claim 13 further comprising:
    polling cassettes of the apparatus; and
    determining whether or not a cassette is in need of refilling by determining if a quantity of the medication in the cassette is below a low level limit.

19. The method of claim 13 further comprising the step of advancing the dose of medication out of a cassette, which houses a strip of multiple doses of the medication and which locks to prevent additional medication from being pulled out of the cassette.

20. A method of managing medication at a pharmacy and a medical facility, comprising:
    packing patient-unassigned medication at a pharmacy to a cassette to be used in a administering apparatus located at the medical facility;
    associating data about the medication with the cassette using a computer at the pharmacy;
    transferring the cassette to the medical facility;
    loading the cassette to the administering apparatus, such that the medication is stored in the administering apparatus;
    identifying the loaded cassette at the administering apparatus using a computer of the administering apparatus;
    receiving a medication order at the pharmacy for a patient wherein the medication order includes a dosing regimen specific to a patient; and thereafter
    checking the medication order for interactions with other medications; and thereafter
    updating a patient record to indicate that the patient is to receive the ordered medication from a shared supply of the medication on the administering apparatus, wherein the medication is not assigned to the patient until administered to the patient; and thereafter
    administering from the administering apparatus a dose of the patient-unassigned medication to the patient having the order with the pharmacy according to the patient's dosing regimen; and then
    assigning the dose of the medication to the patient, including updating the patient record to indicate that the dose of the medication was actually administered to the patient,
    net billing for only doses of medication that are actually administered, wherein a patient or third party is prospectively billed for a predetermined quantity of doses of the medication, and the patient or third party is retroactively credited for any unused doses of the predetermined quantity of doses of medication, wherein the unused doses are not withdrawn from the administering apparatus, and the unused doses are not returned to inventory or discarded.

21. A method as set forth in claim 20, further comprising billing for only those doses of medication that are actually administered.

22. A method as set forth in claim 20 wherein the medication is individually packaged in a continuous strip.

23. A method as set forth in claim 20 wherein the associating step includes writing the data to a memory of the cassette at the pharmacy, and the identifying step includes reading the data from the memory of the cassette at the administering apparatus.

24. A medication administering system comprising:
    a medication administering apparatus including a plurality of cassettes holding patient-unassigned medication and an administering computer to track administration of the medication to a plurality of patients;
    a pharmacy computer networked to the administering computer to facilitate filling of medication orders to be administered out of the medication administering apparatus; and
    a prescriber computer networked to the administering computer and providing remote access to patient records stored in memory of the administering computer and to allow a prescriber to remotely generate a new medication order or change an existing medication order or submit a change order to update the existing medication order,
    wherein the cassettes administer the medication on a unit dose basis to a patient having a prescription, and the administering computer assigns the dose of the medication to the patient, so that the system may be used to net bill a payor for only doses actually administered to the patient, wherein a patient or third party is prospectively billed for a predetermined quantity of doses of the medication, and the patient or third party is retroactively credited for any unused doses of the predetermined quantity of doses of medication, wherein unused doses are not withdrawn from the administering apparatus, and the unused doses are not returned to inventory or discarded, and wherein at least one of the computers updates an inventory of the medication responsive to the administration of the dose of the medication, and estimates a date of depletion of the inventory of the medication so that the administering apparatus is stocked based on the estimated date of depletion.

\* \* \* \* \*